United States Patent
Matsumoto et al.

(10) Patent No.: US 12,383,231 B2
(45) Date of Patent: *Aug. 12, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventors: Tsuyoshi Matsumoto, Tokyo (JP); Tomoki Inoue, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 37 days.

This patent is subject to a terminal disclaimer.

(21) Appl. No.: 18/403,668

(22) Filed: Jan. 3, 2024

(65) Prior Publication Data
US 2024/0130712 A1  Apr. 25, 2024
US 2024/0225603 A9  Jul. 11, 2024

Related U.S. Application Data

(63) Continuation of application No. PCT/JP2022/027200, filed on Jul. 11, 2022.

(30) Foreign Application Priority Data

Jul. 28, 2021 (JP) .................................. 2021-123062

(51) Int. Cl.
*A61B 8/00* (2006.01)
*A61B 8/08* (2006.01)

(52) U.S. Cl.
CPC ............ *A61B 8/461* (2013.01); *A61B 8/0891* (2013.01); *A61B 8/4254* (2013.01); *A61B 8/5223* (2013.01)

(58) Field of Classification Search
CPC ..... A61B 8/461; A61B 8/0891; A61B 8/4254; A61B 8/5223; A61B 8/463; A61B 8/00
See application file for complete search history.

(56) References Cited

U.S. PATENT DOCUMENTS

2006/0241435 A1* 10/2006 Koga .................... A61B 8/462
600/437
2009/0187102 A1   7/2009 Di Marco et al.
(Continued)

FOREIGN PATENT DOCUMENTS

JP   2005-323925 A   11/2005
JP   2009-240779 A   10/2009
(Continued)

OTHER PUBLICATIONS

International Search Report issued in PCT/JP2022/027200; mailed Aug. 16, 2022.
(Continued)

*Primary Examiner* — Bo Joseph Peng
(74) *Attorney, Agent, or Firm* — Studebaker Brackett PLLC

(57) ABSTRACT

In an ultrasound diagnostic apparatus and a control method of the ultrasound diagnostic apparatus of the present invention, a posture sensor detects whether an orientation of a monitor is a vertically long posture or a laterally long posture, and a display control unit displays an ultrasound image on a display screen on the basis of the orientation of the monitor. A hidden region detection unit detects whether or not a hidden region that is not displayed on the display screen is present in the ultrasound image, and a blood vessel detection unit detects a blood vessel in the ultrasound image. Then, in a case where it is detected that the hidden region is present and it is detected that the blood vessel is present in the hidden region, an orientation suggestion unit suggests to change the orientation of the monitor. Accordingly, in a case where blood vessel puncture is performed, an appropriate orientation of the monitor for observing the blood vessel in the ultrasound image is suggested to the user.

20 Claims, 10 Drawing Sheets

(56) References Cited

U.S. PATENT DOCUMENTS

2009/0247874 A1    10/2009   Kim
2016/0350503 A1*   12/2016   Jun .................... A61B 8/465
2019/0328317 A1    10/2019   Mochizuki et al.

FOREIGN PATENT DOCUMENTS

| JP | 2010-057562 A | 3/2010 |
| JP | 2013-165923 A | 8/2013 |
| JP | 2017-225645 A | 12/2017 |
| JP | 2019-188005 A | 10/2019 |

OTHER PUBLICATIONS

International Preliminary Report on Patentability (Chapter I) and Written Opinion of the International Searching Authority issued in PCT/JP2022/027200; issued Jan. 18, 2024.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2022/027200 filed on Jul. 11, 2022, which claims priority under 35 U.S.C. § 119(a) to Japanese Patent Application No. 2021-123062 filed on Jul. 28, 2021. The above applications are hereby expressly incorporated by reference, in their entirety, into the present application.

BACKGROUND OF THE INVENTION

1. Field of the Invention

The present invention relates to an ultrasound diagnostic apparatus and a control method of the ultrasound diagnostic apparatus which display an ultrasound image in a display region of a monitor on the basis of an orientation of the monitor.

2. Description of the Related Art

In a case where blood vessel puncture is performed using an ultrasound diagnostic apparatus, a technique is performed which searches an ultrasound image displayed on a monitor for a blood vessel with appropriate size and depth for puncture and placement of a catheter, carefully observes and analyzes whether or not the blood vessel can be safely punctured with a puncture needle, for example, whether or not there is a peripheral tissue such as a nerve, an artery, and an organ around the blood vessel, and whether or not there is a lesion, a blood clot, or the like, and actually performs the puncture with the puncture needle in a case where it is determined that the blood vessel can be safely punctured with the puncture needle.

In a case of searching for the blood vessel with the appropriate size and depth for the puncture and placement of the catheter, a user (examiner) of the ultrasound diagnostic apparatus needs to select one blood vessel from among many blood vessels present in the ultrasound image. However, since display screens of many monitors are rectangular, and a length in an up and down direction (vertical direction) differs from a length in a left and right direction (lateral direction), the ultrasound images are displayed to fit within the display screen in the ultrasound diagnostic apparatus.

For example, in a case where a monitor 41 is changed from a state where a laterally long ultrasound image 71 is displayed in an enlarged manner to fit within a display screen 72 of the monitor 41 in a laterally long posture as illustrated in FIG. 12A, to a vertically long posture by the user, it is common practice to reduce and display the ultrasound image 71 such that the laterally long ultrasound image 71 fits within the display screen 72 of the monitor 41 in the vertically long posture without changing an aspect ratio of the ultrasound image 71, as illustrated in FIG. 12B.

Here, as prior art documents used as references of the present invention, there are ultrasound imaging devices that perform various kinds of processing according to the orientation of the monitor as in JP2005-323925A, JP2010-057562A, and JP2013-165923A.

JP2005-323925A discloses an ultrasound imaging device that detects the rotation of a display unit in the display screen from positional information of a flat panel type display unit measured by a position sensor, and optimizes image information to be displayed on the display screen of the display unit according to the rotation.

JP2010-057562A discloses an ultrasound diagnostic apparatus that detects a posture change of a housing, and controls generation of an ultrasound image according to the posture change of the housing.

JP2013-165923A discloses an ultrasound diagnostic apparatus that detects a posture or a posture change of an apparatus main body, and changes contents of an image to be displayed on a display surface of a portable apparatus main body on the basis of the posture or the posture change of the apparatus main body.

SUMMARY OF THE INVENTION

However, even though the user wants to check a blood vessel by displaying an ultrasound image in an enlarged manner in a case of performing the blood vessel puncture, in the ultrasound diagnostic apparatus in the related art, the ultrasound image is displayed in a reduced manner in some cases. Therefore, particularly in a case where the apparatus main body is a handheld terminal device such as a smartphone or a tablet personal computer (PC), there is a problem in that it is difficult to observe the blood vessels in the ultrasound image that is displayed in a reduced manner on the display screen.

On the other hand, in a case where the monitor is changed from a state where laterally long ultrasound image is displayed on the display screen of the monitor in the laterally long posture to the vertically long posture by the user without changing the aspect ratio and magnification ratio of the ultrasound image, depending on the difference between the aspect ratio of the display screen and the aspect ratio of the ultrasound image, a partial region of the ultrasound image in a width direction protrudes from the display screen, so that a hidden region of the ultrasound image which is not displayed on the display screen is generated in some cases.

In this case, even though a blood vessel is present in the hidden region, the user observes the ultrasound image in the display screen of the monitor in the vertically long posture, and thus the blood vessel in the hidden region is overlooked in some cases.

Therefore, an object of the present invention is to provide an ultrasound diagnostic apparatus and a control method of the ultrasound diagnostic apparatus which can suggest to a user an appropriate orientation of a monitor for observing a blood vessel in an ultrasound image in a case of performing blood vessel puncture.

In order to achieve the object, an aspect of the present invention provides an ultrasound diagnostic apparatus including a monitor which has a rectangular display screen, and of which an orientation is changeable to a vertically long posture or a laterally long posture; a posture sensor that detects whether the orientation of the monitor is the vertically long posture or the laterally long posture; a display control unit that displays an ultrasound image on the display screen on the basis of the orientation of the monitor; a hidden region detection unit that detects whether or not a hidden region that is not displayed on the display screen is present in the ultrasound image; a blood vessel detection unit that detects a blood vessel in the ultrasound image; and an orientation suggestion unit that suggests to change the orientation of the monitor in a case where it is detected that the hidden region is present and it is detected that the blood vessel is present in the hidden region.

It is preferable that the hidden region detection unit detects whether or not the hidden region is present on the basis of at least one of an aspect ratio of the display screen, an aspect ratio of the ultrasound image, a magnification ratio of the ultrasound image, or the orientation of the monitor.

It is preferable that, in a case where it is detected that the hidden region is present, the blood vessel detection unit detects a blood vessel in the hidden region.

In addition, it is preferable that the display control unit performs control such that the ultrasound image is displayed by being enlarged until a size of the ultrasound image in a depth direction matches a size of the display screen in an up and down direction without changing an aspect ratio of the ultrasound image, regardless of the orientation of the monitor, and in a case where a partial region of the ultrasound image in a width direction is not displayed on the display screen, the hidden region detection unit detects that the hidden region is present in a part of the ultrasound image in the width direction.

It is preferable that the display control unit performs control such that the ultrasound image is displayed by being enlarged until a size of the ultrasound image in a width direction matches a size of the display screen in a left and right direction without changing an aspect ratio of the ultrasound image, regardless of the orientation of the monitor, and in a case where a partial region of the ultrasound image in a depth direction is not displayed on the display screen, the hidden region detection unit detects that the hidden region is present in a part of the ultrasound image in the depth direction.

In addition, it is preferable that an aspect ratio of the display screen is the same as an aspect ratio of a laterally long ultrasound image, in a case where the monitor is changed between the laterally long posture and the vertically long posture, the display control unit performs control such that the ultrasound image is displayed on the display screen without changing the aspect ratio and a magnification ratio of the ultrasound image, and in a case where it is detected that the monitor is changed from the laterally long posture to the vertically long posture and a partial region of the ultrasound image in a width direction is not displayed on the display screen, the hidden region detection unit detects that the hidden region is present in a part of the ultrasound image in the width direction.

In addition, it is preferable that an aspect ratio of the display screen is the same as an aspect ratio of a vertically long ultrasound image, in a case where the monitor is changed between the vertically long posture and the laterally long posture, the display control unit performs control such that the ultrasound image is displayed on the display screen without changing the aspect ratio and a magnification ratio of the ultrasound image, and in a case where it is detected that the monitor is changed from the vertically long posture to the laterally long posture and a partial region of the ultrasound image in a depth direction is not displayed on the display screen, the hidden region detection unit detects that the hidden region is present in a part of the ultrasound image in the depth direction.

In addition, it is preferable that the display control unit performs control such that, in a case where it is detected that the monitor is in the vertically long posture, the ultrasound image is displayed by being enlarged until a size of the ultrasound image in a depth direction matches a size of the display screen in an up and down direction without changing an aspect ratio of the ultrasound image, and in a case where it is detected that the monitor is in the laterally long posture, the ultrasound image is displayed by being enlarged until a size of the ultrasound image in a width direction matches a size of the display screen in a left and right direction without changing the aspect ratio of the ultrasound image, and in a case where it is detected that the monitor is in the vertically long posture and a partial region of the ultrasound image in the width direction is not displayed on the display screen, the hidden region detection unit detects that the hidden region is present in a part of the ultrasound image in the width direction, and in a case where it is detected that the monitor is in the laterally long posture and a partial region of the ultrasound image in the depth direction is not displayed on the display screen, the hidden region detection unit detects that the hidden region is present in a part of the ultrasound image in the depth direction.

In addition, it is preferable that the hidden region detection unit detects whether or not the hidden region is generated in each of a case where the monitor is in the vertically long posture and a case where the monitor is in the laterally long posture, in a case where it is detected that the hidden region is generated in each of the case where the monitor is in the vertically long posture and the case where the monitor is in the laterally long posture, the blood vessel detection unit detects a blood vessel in the hidden region in each of the case where the monitor is in the vertically long posture and the case where the monitor is in the laterally long posture, and in a case where it is detected that the monitor is in one orientation of the vertically long posture or the laterally long posture and the number of blood vessels in the hidden region in a case where the monitor is in the other orientation is smaller than the number of blood vessels in the hidden region in a case where the monitor is in the one orientation, the orientation suggestion unit suggests to change the monitor to the other orientation.

In addition, it is preferable that the hidden region detection unit detects whether or not the hidden region is generated in each of a case where the monitor is in the vertically long posture and a case where the monitor is in the laterally long posture, in a case where it is detected that the hidden region is generated in each of the case where the monitor is in the vertically long posture and the case where the monitor is in the laterally long posture and it is detected that a blood vessel is present in each of a display region displayed on the display screen and the hidden region of the ultrasound image, the blood vessel detection unit discriminates whether a type of the blood vessel in each of the display region and the hidden region is an artery or a vein, and the orientation suggestion unit suggests to change the orientation of the monitor on the basis of the type of the blood vessel in the display region and the type of the blood vessel in the hidden region.

In addition, it is preferable that, in a case where it is detected that the monitor is in the laterally long posture and it is discriminated that a vein is present in the display region in a case where the monitor is in the laterally long posture and that an artery is present in the hidden region in a case where the monitor is in the laterally long posture, the orientation suggestion unit suggests to change the monitor to the vertically long posture.

In addition, it is preferable that, in a case where it is detected that the monitor is in the vertically long posture and it is discriminated that a vein is present in the display region in a case where the monitor is in the vertically long posture and that a vein is present in the hidden region in a case where the monitor is in the vertically long posture, the orientation suggestion unit suggests to change the monitor to the laterally long posture.

In addition, it is preferable that, in a case where it is discriminated that an artery is present in the display region, the blood vessel detection unit discriminates whether or not a vein is present in the hidden region in each of a case where the monitor is in one orientation of the vertically long posture or the laterally long posture and a case where the monitor is in the other orientation, on the basis of a position of the artery in the display region and an anatomical structure around the artery in the display region, and in a case where it is discriminated that no vein is present in the hidden region in a case where the monitor is in the one orientation and that a vein is present in the hidden region in a case where the monitor is in the other orientation, the orientation suggestion unit suggests to change the monitor to the other orientation.

In addition, it is preferable that the display control unit performs control such that the ultrasound image is enlarged and displayed without changing an aspect ratio of the ultrasound image according to an instruction from a user, and in a case where the ultrasound image is enlarged and displayed so that a partial region of the ultrasound image in a depth direction is not displayed on the display screen, the hidden region detection unit detects that the hidden region is present in a part of the ultrasound image in the depth direction, and in a case where the ultrasound image is enlarged and displayed so that a partial region of the ultrasound image in a width direction is not displayed on the display screen, the hidden region detection unit detects that the hidden region is present in a part of the ultrasound image in the width direction.

Further, another aspect of the present invention provides a control method of an ultrasound diagnostic apparatus including a monitor which has a rectangular display screen, and of which an orientation is changeable to a vertically long posture or a laterally long posture, the control method including a step of detecting whether the orientation of the monitor is the vertically long posture or the laterally long posture, via a posture sensor; a step of displaying an ultrasound image on the display screen on the basis of the orientation of the monitor, via a display control unit; a step of detecting whether or not a hidden region that is not displayed on the display screen is present in the ultrasound image; a step of detecting a blood vessel in the ultrasound image, via a blood vessel detection unit; and a step of suggesting to change the orientation of the monitor in a case where it is detected that the hidden region is present and it is detected that the blood vessel is present in the hidden region, via an orientation suggestion unit.

In the present invention, in a case where it is detected that a hidden region is present in the ultrasound image and it is detected that a blood vessel is present in the hidden region, the user is suggested to change the orientation of the monitor.

Accordingly, according to the present invention, it is possible to suggest to the user an appropriate orientation of the monitor for observing the blood vessel in the ultrasound image in a case of performing the blood vessel puncture. On the other hand, in accordance with this suggestion, the user can display the blood vessel in the hidden region on the display screen of the monitor by changing the orientation of the monitor, and can check the blood vessel, and thus, the blood vessel puncture can be performed safely and reliably.

DESCRIPTION OF THE PREFERRED EMBODIMENTS

Hereinafter, an ultrasound diagnostic apparatus and a control method of the ultrasound diagnostic apparatus according to the present invention will be described in detail on the basis of preferred embodiments illustrated in the accompanying drawings.

Figure 1:
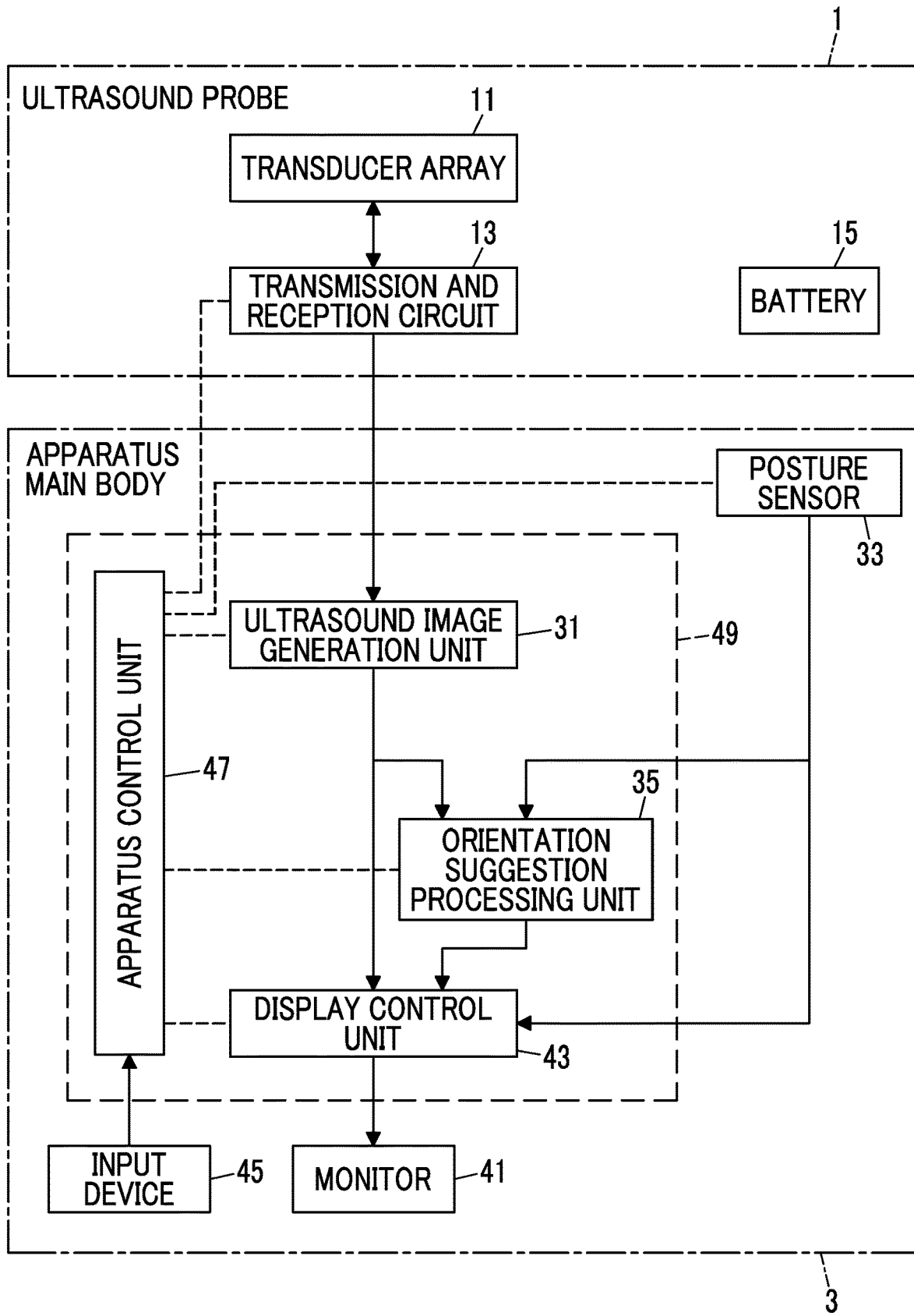
FIG. 1 is a block diagram of an embodiment illustrating a configuration of an ultrasound diagnostic apparatus of the present invention.

FIG. 1 is a block diagram of an embodiment illustrating a configuration of an ultrasound diagnostic apparatus of the present invention. The ultrasound diagnostic apparatus illustrated in FIG. 1 is a handheld ultrasound diagnostic apparatus, and includes an ultrasound probe 1, and an apparatus main body 3 connected to the ultrasound probe 1. The ultrasound diagnostic apparatus of the present embodiment is realized by the ultrasound probe 1, the handheld apparatus main body 3, and an ultrasound diagnosis application program running on the apparatus main body 3.

The ultrasound probe 1 scans an examination location of a subject using an ultrasound beam, and outputs a sound ray signal corresponding to an ultrasound image of the examination location. As illustrated in FIG. 1, the ultrasound probe 1 includes a transducer array 11, a transmission and reception circuit 13, and a battery 15. The transducer array 11 and the transmission and reception circuit 13 are bidirectionally connected to each other, and an apparatus control unit 47 of the apparatus main body 3, which will be described later, is connected to the transmission and reception circuit 13.

The transducer array 11 has a plurality of ultrasonic transducers arranged in a one-dimensional or two-dimensional manner. According to a drive signal supplied from the transmission and reception circuit 13, each of the transducers transmits an ultrasonic wave and receives a reflected wave from the subject to output an analog reception signal.

For example, each transducer is formed by using an element in which electrodes are formed at both ends of a piezoelectric body consisting of piezoelectric ceramic typified by lead zirconate titanate (PZT), a polymer piezoelectric element typified by poly vinylidene di fluoride (PVDF), piezoelectric single crystal typified by lead magnesium niobate-lead titanate (PMN-PT), or the like.

Figure 2:
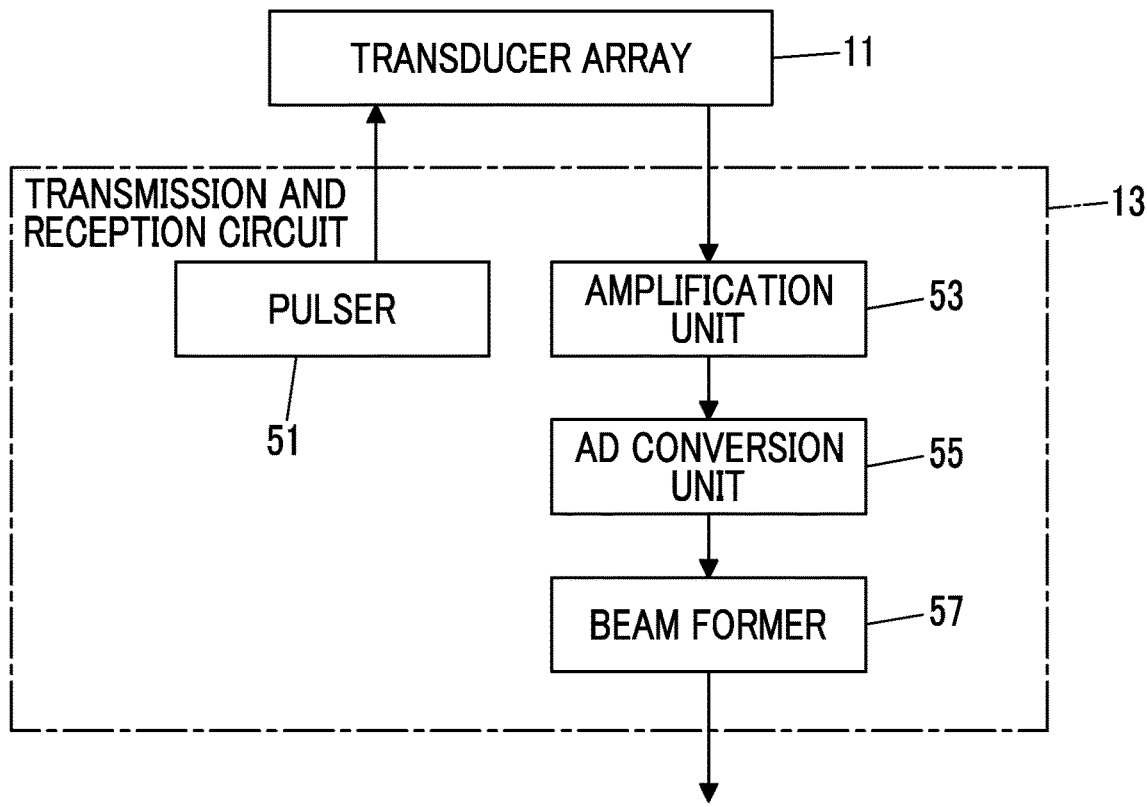
FIG. 2 is a block diagram of an embodiment illustrating a configuration of a transmission and reception circuit.

The transmission and reception circuit 13 causes the transducer array 11 to transmit the ultrasound beam, and performs reception focusing processing on the reception signal output from the transducer array 11 that has received the ultrasound echo to generate a sound ray signal, under the control of the apparatus control unit 47. As illustrated in FIG. 2, the transmission and reception circuit 13 has a pulser 51 connected to the transducer array 11, and an amplification unit 53, an analog digital (AD) conversion unit 55, and a beam former 57 that are sequentially connected in series from the transducer array 11.

The pulser 51 includes, for example, a plurality of pulse generators, and the pulser 51 performs transmission focusing processing of adjusting the amount of delay of each drive signal so that ultrasonic waves transmitted from the plurality of transducers of the transducer array 11 form an ultrasound beam on the basis of a transmission delay pattern selected by the apparatus control unit 47, and supplying the obtained signals to the plurality of transducers. By this transmission focusing processing, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 53.

The amplification unit 53 amplifies the signals input from each transducer constituting the transducer array 11, and transmits the amplified signals to the AD conversion unit 55. The AD conversion unit 55 converts the analog signal transmitted from the amplification unit 53 into digital reception data, and outputs the reception data to the beam former 57.

The beam former 57 performs reception focusing processing in which addition is performed by giving delays to respective pieces of the reception data converted by the AD conversion unit 55 according to a sound speed distribution or a sound speed set on the basis of a reception delay pattern selected by the apparatus control unit 47. Through the reception focusing processing, a sound ray signal in which each piece of the reception data converted by the AD conversion unit 55 is phased and added and the focus of the ultrasound echo is narrowed is generated.

The battery 15 is built in the ultrasound probe 1, and supplies power to each circuit of the ultrasound probe 1.

Next, the apparatus main body 3 generates and displays the ultrasound image of the examination location of the subject on the basis of the sound ray signal generated by the ultrasound probe 1. The apparatus main body 3 is, for example, a handheld terminal device such as a smartphone or a tablet personal computer (PC), and includes an ultrasound image generation unit 31, a posture sensor 33, an orientation suggestion processing unit 35, a monitor 41, a display control unit 43, an input device 45, and the apparatus control unit 47 as illustrated in FIG. 1.

The ultrasound image generation unit 31 is connected to the transmission and reception circuit 13 of the ultrasound probe 1, and the display control unit 43 and the monitor 41 are sequentially connected to the ultrasound image generation unit 31. Each of the orientation suggestion processing unit 35 and the display control unit 43 is connected to the posture sensor 33. In addition, the orientation suggestion processing unit 35 is connected to the ultrasound image generation unit 31. The apparatus control unit 47 is connected to the ultrasound image generation unit 31, the posture sensor 33, the orientation suggestion processing unit 35, and the display control unit 43, and the apparatus control unit 47 is connected to the input device 45.

The ultrasound probe 1 and the apparatus main body 3 are wirelessly connected by wireless communication such as Wireless Fidelity (Wi-Fi), or are connected in a wired manner by wired communication such as a Universal Serial Bus (USB) cable.

Figure 3:
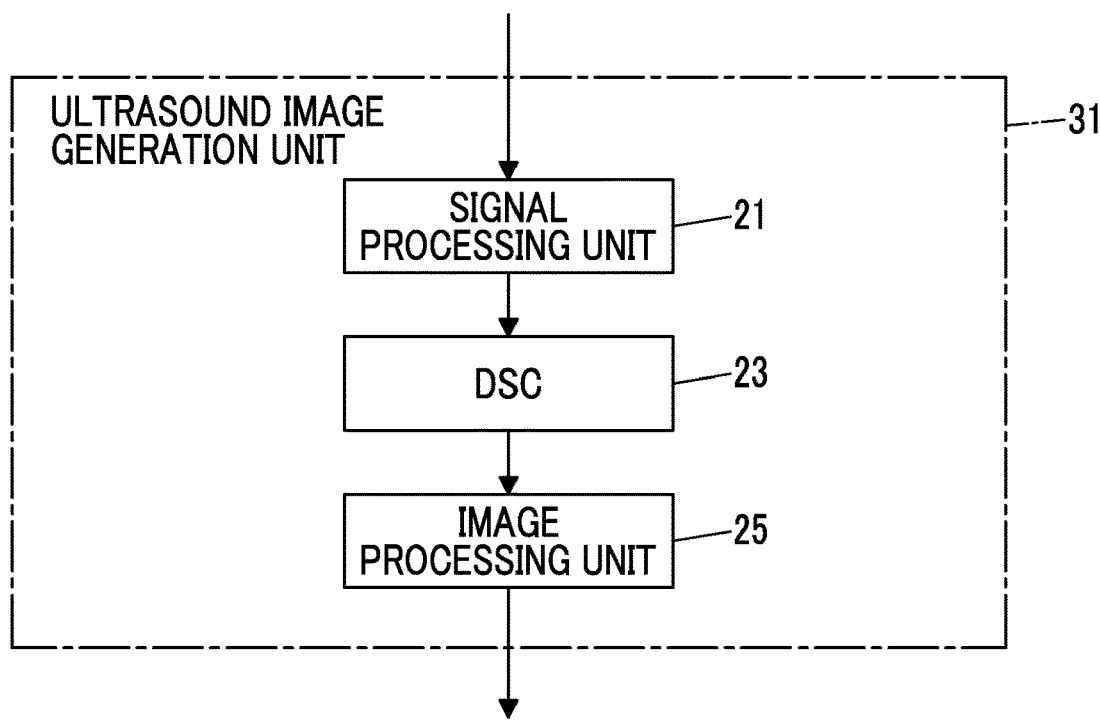
FIG. 3 is a block diagram of an embodiment illustrating a configuration of an ultrasound image generation unit.

The ultrasound image generation unit 31 generates the ultrasound image (ultrasound image signal) of the examination location of the subject, from the reception signal obtained by performing transmission and reception of the ultrasound beams with respect to the examination location of the subject using the ultrasound probe 1 (more precisely, transducer array 11), in other words, from the sound ray signal generated from the reception signal by the transmission and reception circuit 13, under the control of the apparatus control unit 47. As illustrated in FIG. 3, the ultrasound image generation unit 31 has a configuration in which a signal processing unit 21, a digital scan converter (DSC) 23, and an image processing unit 25 are sequentially connected in series.

The signal processing unit 21 generates image information data corresponding to the ultrasound image on the basis of the sound ray signal generated by the transmission and reception circuit 13. More specifically, the signal processing unit 21 generates the image information data representing tomographic image information regarding tissues inside the subject, by performing envelope detection processing after signal processing, for example, correcting the attenuation of the sound ray signal generated by the beam former 57 of the transmission and reception circuit 13, which is caused by the propagation distance according to the depth of the reflection position of the ultrasonic wave.

The DSC 23 raster-converts the image information data generated by the signal processing unit 21 into an image signal according to a normal television signal scanning method.

The image processing unit 25 performs various kinds of image processing such as brightness correction, gradation correction, sharpness correction, image size correction, refresh rate correction, scanning frequency correction, and color correction according to a display format of the monitor 41, on the image signal input from the DSC 23 to generate the ultrasound image, and then outputs the ultrasound image on which the image processing has been performed, to the display control unit 43.

The monitor (display unit) 41 has a rectangular display screen, is configured such that the orientation can be changed to a vertically long posture in which the display screen is in a vertically long state or a laterally long posture in which the display screen is in a laterally long state by the user rotating the apparatus main body 3 by 90 degrees around an axis perpendicular to the display screen, and displays various kinds of information under the control of the display control unit 43.

The monitor 41 is not particularly limited, but for example, a liquid crystal display (LCD), an organic electroluminescence (EL) display, and the like can be exemplified.

The posture sensor 33 detects whether the orientation (posture) of the monitor 41, that is, the orientation (posture) of the apparatus main body 3 in the present embodiment is the vertically long posture or the laterally long posture, under the control of the apparatus control unit 47.

The posture sensor 33 is not particularly limited as long as the orientation of the monitor 41 can be detected, and examples of the posture sensor 33 include an acceleration sensor that detects the motion of the apparatus main body 3, a gravity sensor that detects the gravity, and a gyro sensor that detects the rotation of the apparatus main body 3.

Figure 4:
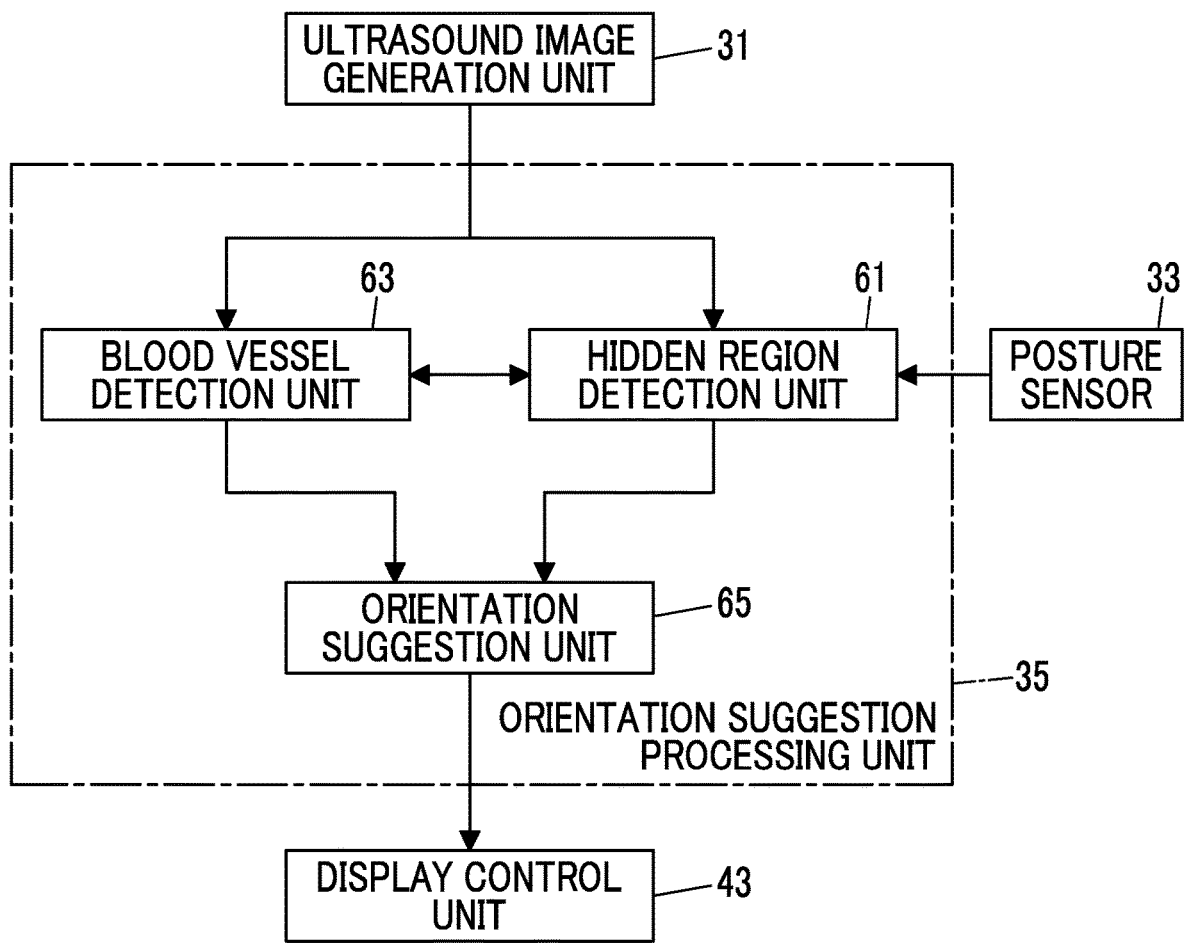
FIG. 4 is a block diagram of an embodiment illustrating a configuration of an orientation suggestion processing unit.

The orientation suggestion processing unit 35 performs various kinds of processing for suggesting to change the orientation of the monitor 41, under the control of the apparatus control unit 47. As illustrated in FIG. 4, the orientation suggestion processing unit 35 has a hidden region detection unit 61, a blood vessel detection unit 63, and an orientation suggestion unit 65.

Each of the hidden region detection unit 61 and the blood vessel detection unit 63 is connected to the ultrasound image generation unit 31. The hidden region detection unit 61 is connected to the posture sensor 33, and the hidden region detection unit 61 and the blood vessel detection unit 63 are bidirectionally connected. The orientation suggestion unit 65 is connected to each of the hidden region detection unit 61 and the blood vessel detection unit 63, and the display control unit 43 is connected to the orientation suggestion unit 65.

The hidden region detection unit 61 detects whether or not a hidden region that is not displayed on the display screen is present in the ultrasound image.

The method of detecting the hidden region is not particularly limited, but, for example, the hidden region detection unit 61 can detect whether or not a hidden region is present on the basis of at least one of the aspect ratio of the display screen, the aspect ratio of the ultrasound image, the magnification ratio of the ultrasound image, or the orientation of the monitor 41 detected by the posture sensor 33.

The aspect ratio of the display screen is a height to width ratio of the display screen of the rectangular monitor 41, and the aspect ratio of the ultrasound image is a height to width ratio of the ultrasound image. These aspect ratios are input from the apparatus control unit 47 to the hidden region detection unit 61, for example.

The magnification ratio of the ultrasound image is magnification ratio of the ultrasound image displayed on the display screen of the monitor 41, and is inputted from the display control unit 43 to the hidden region detection unit 61 via the apparatus control unit 47, for example.

The hidden region is a region of the ultrasound image, which is not displayed on the display screen in a case where the ultrasound image is displayed on the display screen of the monitor 41. On the other hand, a region of the ultrasound image, which is displayed on the display screen, is referred to as a display region.

The blood vessel detection unit 63 detects a blood vessel in the ultrasound image by analyzing the ultrasound image. In addition, in a case where it is detected that a blood vessel is present in the ultrasound image, the blood vessel detection unit 63 discriminates whether the type of the blood vessel is an artery or a vein.

The blood vessel detection unit 63 detects short-axis views of all the blood vessels in the ultrasound image, for example. The short-axis view of the blood vessel is an image of a cross section obtained by slicing the blood vessel in a cross-sectional direction perpendicular to a running direction of the blood vessel. Therefore, the short-axis view of the blood vessel represents a region (blood vessel region) of the cross section of the blood vessel in the cross-sectional direction.

The method of detecting the blood vessel is not particularly limited as long as the blood vessel in the ultrasound image can be detected. The blood vessel detection unit 63 can use various methods for detecting the short-axis view of the blood vessel from the ultrasound image, such as a method of using a blood vessel determination model by machine learning, and a method of using template matching, as the image analysis processing for detecting the blood vessel shown in the ultrasound image. In addition, the blood vessel can also be detected by measuring a blood flow using the Doppler method.

The method of discriminating the type of the blood vessel is not particularly limited, but whether the blood vessel is an artery or a vein can be identified on the basis of the roundness of the short-axis view of the blood vessel, for example. Since arteries have a high internal pressure and veins have a lower internal pressure than arteries, a blood vessel of which the roundness is equal to or greater than a predetermined threshold value can be identified as an artery, and a blood vessel of which the roundness is less than a predetermined threshold value can be identified as a vein. In addition, on the basis of the anatomical structure regarding the tissues around the blood vessel included in the ultrasound image, whether or not the blood vessel is an artery or a vein can be identified from the fact that the arteries and veins run in a predetermined direction around the tissues. Furthermore, the type of the blood vessel can also be discriminated by measuring the blood flow using the Doppler method.

Note that the blood vessel detection unit 63 may detect the blood vessel in the ultrasound image, that is, the blood vessel in the hidden region in a case where the hidden region detection unit 61 detects that a hidden region is present. Accordingly, only in a case where it is detected that a hidden region is present, a blood vessel in the hidden region is detected. Therefore, there is no need to wastefully perform blood vessel detection processing in a case where it is not detected that a hidden region is present, and thus, it is possible to reduce the processing time and the cost.

In addition, the blood vessel detection unit 63 may detect the blood vessel in the ultrasound image for each ultrasound image of one frame, may detect the blood vessel in the ultrasound image once for every ultrasound images of a plurality of frames, or may obtain an average value of the blood vessels detected from the ultrasound images of the plurality of frames.

In a case where the hidden region detection unit 61 detects that a hidden region is present and the blood vessel detection unit 63 detects that a blood vessel is present in the hidden region, the orientation suggestion unit 65 suggests to change the orientation of the monitor 41, that is, to change the orientation from the vertically long posture to the laterally long posture or from the laterally long posture to the vertically long posture. In other words, the orientation suggestion unit 65 prompts the user to change the orientation of the monitor 41 by rotating the apparatus main body 3 by 90 degrees around an axis perpendicular to the display screen of the monitor 41.

Although not particularly limited, for example, the orientation suggestion unit 65 may display a message for suggesting to change the orientation of the monitor 41, on the monitor 41, or may output the message from a speaker (not illustrated) as an audio, under the control of the display control unit 43. In addition, the orientation suggestion unit 65 may suggest to change the orientation of the monitor 41 by vibrating the apparatus main body 3 using the transducer (not illustrated). Furthermore, the orientation suggestion unit 65 may perform two or more methods described above in combination.

The display control unit 43 displays various kinds of information on the monitor 41 under the control of the apparatus control unit 47.

For example, the display control unit 43 displays the ultrasound image on the display screen of the monitor 41 on the basis of the orientation of the monitor 41. In a case where the monitor 41 is in the laterally long posture, the ultrasound image is displayed in a vertically long posture on the display screen of the monitor 41 in the laterally long posture. On the other hand, in a case where the monitor 41 is in the vertically long posture, the ultrasound image is displayed in the vertically long posture on the display screen of the monitor 41 in the vertically long posture. In this manner, even in a case where the monitor 41 is in the laterally long posture or in the vertically long posture, the ultrasound image is displayed always in the vertically long posture on the display screen of the monitor 41.

In addition, in a case where the posture of the monitor 41 is changed from the laterally long posture to the vertically long posture, or in a case where the posture of the monitor 41 is changed from the vertically long posture to the laterally long posture, the ultrasound image is rotated by 90 degrees around the axis perpendicular to the display screen so as to be displayed always in the vertically long posture on the display screen of the monitor 41.

Furthermore, the display control unit 43 performs control such that the ultrasound image is displayed on the display screen in an enlarged manner on the basis of the orientation of the monitor 41 or according to an instruction from the user.

The input device 45 receives various instructions input from the user. The input device 45 is not particularly limited, but includes, for example, various buttons, and a touch panel or the like which is provided on the display screen of the monitor 41 and through which various instructions are input by the user's touch operation.

The apparatus control unit 47 controls the ultrasound probe 1 and each unit of the apparatus main body 3 on the basis of a program stored in advance and an instruction or the like of the user input from the input device 45.

In the present embodiment, the ultrasound image generation unit 31, the orientation suggestion processing unit 35, the display control unit 43, and the apparatus control unit 47 constitute a processor 49.

Figure 5:
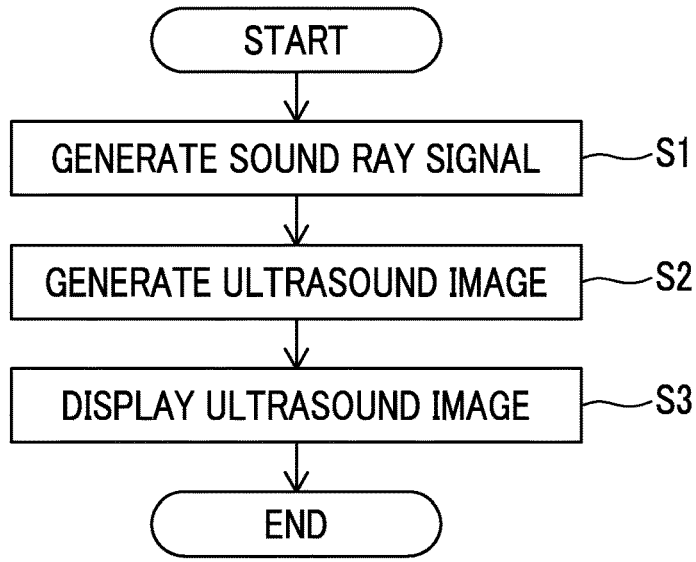
FIG. 5 is a flowchart of an embodiment illustrating an operation of an ultrasound diagnostic apparatus in a case of generating an ultrasound image.

Next, the operation of the ultrasound diagnostic apparatus in a case of generating the ultrasound image will be described with reference to the flowchart of FIG. 5.

First, in a case where the ultrasound image is generated, in a state where the ultrasound probe 1 is in contact with the examination location of the subject, the transmission of the ultrasonic waves is started and the sound ray signal is generated by the transmission and reception circuit 13, under the control of the apparatus control unit 47 (Step S1).

That is, the ultrasound beams are transmitted to the examination location of the subject from a plurality of transducers of the transducer array 11 according to the drive signals from the pulser 51.

Ultrasound echoes from the examination location based on the ultrasound beams transmitted from the pulser 51 are received by each transducer of the transducer array 11, and the reception signal as an analog signal is output from each transducer of the transducer array 11, which has received the ultrasound echo.

The reception signal output from each transducer of the transducer array 11 is amplified by the amplification unit 53, and is subjected to AD conversion by the AD conversion unit 55, and thereby the reception data is acquired.

Then, by performing the reception focusing processing on the reception data by the beam former 57, the sound ray signal is generated.

Subsequently, under the control of the apparatus control unit 47, the ultrasound image of the examination location of the subject is generated by the ultrasound image generation unit 31 on the basis of the sound ray signal generated by the beam former 57 of the transmission and reception circuit 13 (Step S2).

That is, the sound ray signal generated by the beam former 57 is subjected to various kinds of signal processing by the signal processing unit 21, and the image information data representing tomographic image information regarding tissues inside the subject is generated.

Then, the image information data generated by the signal processing unit 21 is raster-converted by the DSC 23, and is further subjected to various kinds of image processing by the image processing unit 25, and thus the ultrasound image is generated.

Subsequently, under the control of the apparatus control unit 47, predetermined processing is performed on the ultrasound image generated by the image processing unit 25, by the display control unit 43, and the processed ultrasound image is displayed on the monitor 41 (Step S3).

Figure 6:
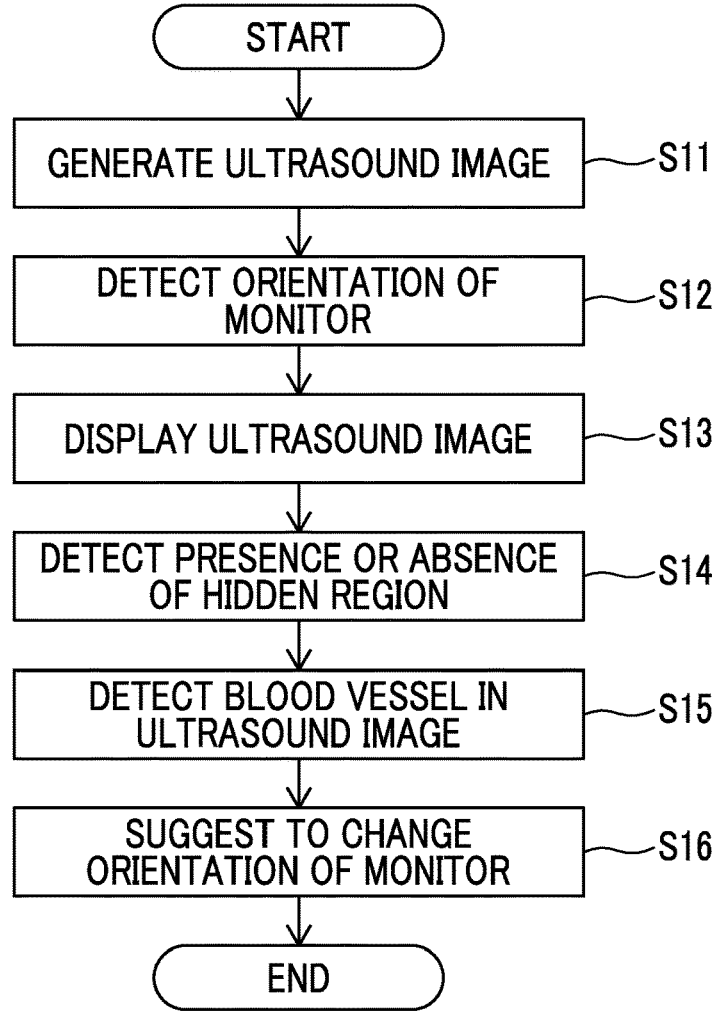
FIG. 6 is a flowchart of an embodiment illustrating an operation of an ultrasound diagnostic apparatus in a case where a user searches for a blood vessel in an ultrasound image when performing blood vessel puncture.

Next, the operation of the ultrasound diagnostic apparatus in a case where the user searches for the blood vessel in the ultrasound image when performing the blood vessel puncture will be described with reference to the flowchart illustrated in FIG. 6.

In a case where the blood vessel puncture is performed, the user selects a blood vessel puncture mode from examination menus displayed on the monitor 41 by a touch operation, for example.

Subsequently, the user searches for the blood vessel (vein) as a puncture target while moving the ultrasound probe 1 in a state where the ultrasound probe 1 is in contact with the examination location of the subject by setting the monitor 41 in the vertically long posture or the laterally long posture.

Accordingly, as described above, the ultrasound image including the short-axis view of the blood vessel in the examination location of the subject is generated by the ultrasound image generation unit 31 (Step S11).

In addition, whether the orientation of the monitor 41 is the vertically long posture or the laterally long posture is detected by the posture sensor 33, under the control of the apparatus control unit 47 (Step S12).

Subsequently, the ultrasound image is displayed on the display screen of the monitor 41 by the display control unit 43 on the basis of the orientation of the monitor 41 (Step S13).

On the other hand, various kinds of processing for suggesting to change the orientation of the monitor 41 are performed by the orientation suggestion processing unit 35.

That is, whether or not a hidden region is present in the ultrasound image is detected by the hidden region detection unit 61 on the basis of the aspect ratio of the display screen, the aspect ratio of the ultrasound image, the magnification ratio of the ultrasound image, and the orientation of the monitor 41 (Step S14).

In addition, the blood vessel in the ultrasound image is detected by the blood vessel detection unit 63 (Step S15). In this case, the blood vessel in the display region detected by the blood vessel detection unit 63 may be displayed in an emphasis manner by the display control unit 43.

Then, in a case where it is detected that a hidden region is present and it is detected that a blood vessel is present in the hidden region, the orientation suggestion unit 65 suggests to change the orientation of the monitor 41 (Step S16).

Accordingly, in a case where the orientation of the monitor 41 is changed by the user, the changed orientation of the monitor 41 is detected by the posture sensor 33, and the ultrasound image is displayed on the display screen by the display control unit 43 on the basis of the changed orientation of the monitor 41.

On the other hand, in a case where the orientation of the monitor 41 is not changed by the user, the display of the ultrasound image is not changed.

In this manner, in the ultrasound diagnostic apparatus, in a case where it is detected that a hidden region is present in the ultrasound image and it is detected that a blood vessel is present in the hidden region, the user is suggested to change the orientation of the monitor 41.

Accordingly, with the ultrasound diagnostic apparatus, it is possible to suggest to the user an appropriate orientation of the monitor 41 for observing the blood vessel in the ultrasound image in a case of performing the blood vessel puncture. On the other hand, in accordance with this suggestion, the user can display the blood vessel in the hidden region on the display screen of the monitor 41 by changing the orientation of the monitor 41, and can check the blood vessel, and thus, the blood vessel puncture can be performed safely and reliably.

Note that, various kinds of processing for the orientation suggestion processing unit 35 to suggest to change the orientation of the monitor 41 may be performed in a live mode, or may be performed in a freeze mode.

Next, several specific examples in a case where a hidden region is generated in the ultrasound image will be described.

Figure 7A:
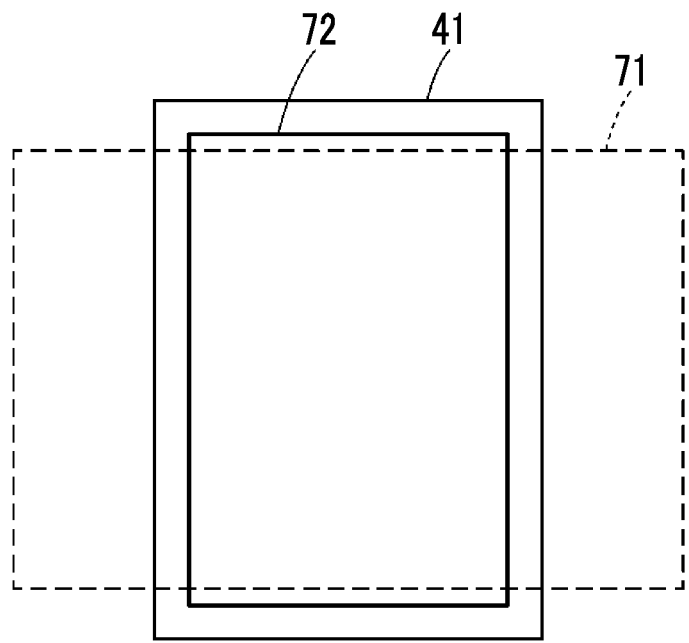
FIG. 7A is a conceptual diagram illustrating a positional relationship between a display screen in a case where a monitor is in a vertically long posture and an ultrasound image displayed on the display screen, in a first specific example.
Figure 7B:
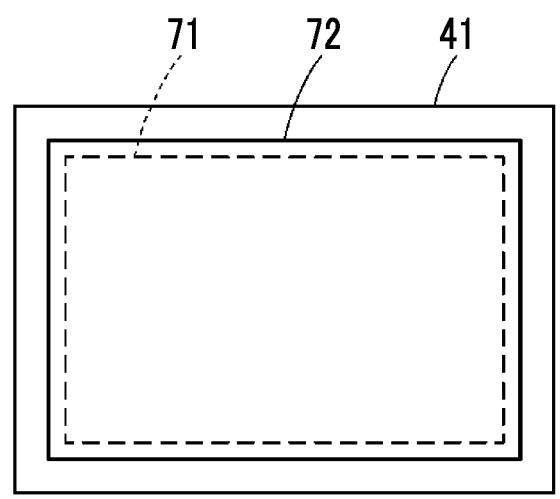
FIG. 7B is a conceptual diagram illustrating a positional relationship between a display screen in a case where a monitor is in a laterally long posture and an ultrasound image displayed on the display screen, in the first specific example.

FIGS. 7A and 7B are conceptual diagrams of a first specific example illustrating a positional relationship between the display screen and the ultrasound image displayed on the display screen.

In the first specific example, the display control unit 43 performs control such that the ultrasound image is displayed by being enlarged until the size of the ultrasound image in the depth direction matches the size of the display screen in the up and down direction without changing the aspect ratio of the ultrasound image, regardless of the orientation of the monitor 41.

FIG. 7A illustrates a positional relationship between a display screen 72 in a case where the monitor 41 is in the vertically long posture and an ultrasound image 71 displayed on the display screen 72, in the first specific example. In this case, by the display control unit 43, the ultrasound image is displayed by being enlarged until the size of the laterally long ultrasound image in the depth direction matches the size of the display screen in the up and down direction without changing the aspect ratio of the ultrasound image.

In FIG. 7A, the ultrasound image 71 is indicated by a dashed line, and the display screen is indicated by a solid line. The same applies to FIGS. 7B, 8A, 8B, 9A, 9B, 10A, 10B, 11A, and 11B described below.

In a case where the ultrasound image is displayed as illustrated in FIG. 7A, depending on the difference between the aspect ratio of the display screen and the aspect ratio of the ultrasound image, a partial region of the ultrasound image in the width direction is not displayed on the display screen in some cases. FIG. 7A illustrates an example of a case where a partial region on both sides of the ultrasound image in the width direction is not displayed on the display screen, that is, a case where a hidden region is present in a part on both sides of the ultrasound image in the width direction.

In this case, the posture sensor 33 detects that the monitor 41 is in the vertically long posture.

On the other hand, as illustrated in FIG. 7A, in a case where a partial region on both sides of the ultrasound image in the width direction is not displayed on the display screen, the hidden region detection unit 61 detects that a hidden region is present in a part on both sides of the ultrasound image in the width direction.

In addition, the blood vessel in the ultrasound image is detected by the blood vessel detection unit 63.

Then, in a case where it is detected that a hidden region is present in a part on both sides of the ultrasound image in the width direction and it is detected that a blood vessel is present in the hidden region, the orientation suggestion unit 65 suggests to change the monitor 41 to the laterally long posture.

Accordingly, in a case where the monitor 41 is changed to the laterally long posture by the user, the posture sensor 33 detects that the changed posture of the monitor 41 is the laterally long posture, and the display control unit 43 displays the ultrasound image on the basis of the monitor 41 in the laterally long posture.

FIG. 7B illustrates a positional relationship between the display screen 72 in a case where the monitor 41 is in the laterally long posture and the ultrasound image 71 displayed on the display screen 72, in the first specific example. In this case, by the display control unit 43, the laterally long ultrasound image is displayed on the display screen without changing the aspect ratio of the ultrasound image. Note that the display control in this case is not particularly limited, and the ultrasound image may be displayed in any manner.

For example, even though there are many blood vessels in the ultrasound image in the width direction, in a case where a partial region of the ultrasound image in the width direction is not displayed on the display screen due to the vertically long posture of the monitor 41, the blood vessel in the partial region of the ultrasound image in the width direction, which is not displayed in a case where the monitor 41 is in the vertically long posture, can be displayed by changing the monitor 41 to the laterally long posture, and therefore, it is possible for the user to easily check the blood vessel in the ultrasound image in the width direction.

Note that, FIG. 7A illustrates an example of a case where the ultrasound image is displayed by being enlarged until the size of the laterally long ultrasound image in the depth direction matches the size of the display screen in the up and down direction of the monitor 41 in the vertically long posture, but the invention is not limited thereto, and can be similarly applied to a case where the ultrasound image is displayed by being enlarged until the size of the laterally long ultrasound image in the depth direction matches the size of the display screen in the up and down direction of the monitor 41 in the laterally long posture.

Figure 8A:
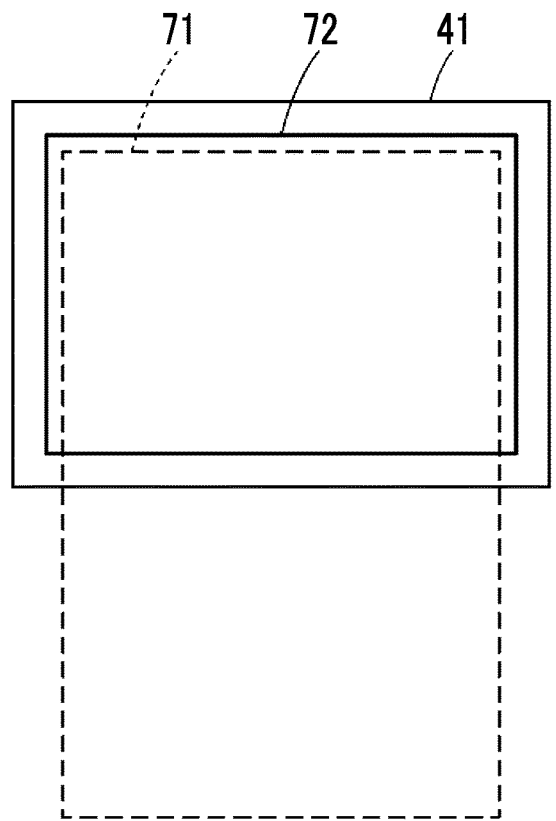
FIG. 8A is a conceptual diagram illustrating a positional relationship between a display screen in a case where a monitor is in a laterally long posture and an ultrasound image displayed on the display screen, in a second specific example.
Figure 8B:
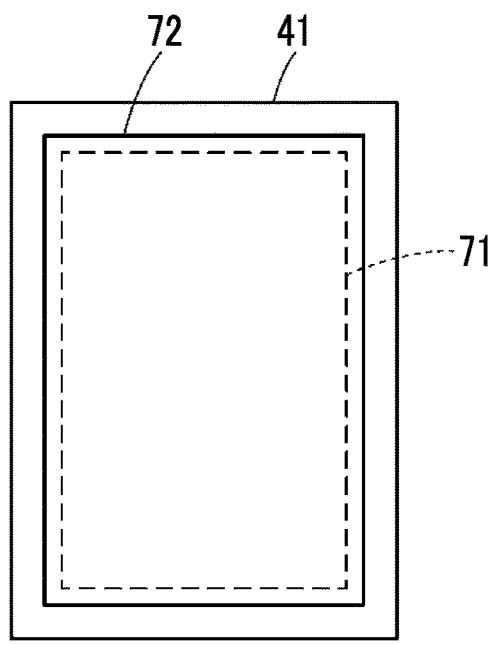
FIG. 8B is a conceptual diagram illustrating a positional relationship between a display screen in a case where a monitor is in a vertically long posture and an ultrasound image displayed on the display screen, in the second specific example.

FIGS. 8A and 8B are conceptual diagrams of a second specific example illustrating a positional relationship between the display screen and the ultrasound image displayed on the display screen.

In the second specific example, the display control unit 43 performs control such that the ultrasound image is displayed by being enlarged until the size of the ultrasound image in the width direction matches the size of the display screen in the left and right direction without changing the aspect ratio of the ultrasound image, regardless of the orientation of the monitor 41.

FIG. 8A illustrates a positional relationship between the display screen 72 in a case where the monitor 41 is in the laterally long posture and the ultrasound image 71 displayed on the display screen 72, in the second specific example. In this case, by the display control unit 43, the ultrasound image is displayed by being enlarged until the size of the vertically long ultrasound image in the width direction matches the size of the display screen in the left and right direction without changing the aspect ratio of the ultrasound image.

Even in a case where the ultrasound image is displayed as illustrated in FIG. 8A, depending on the difference between the aspect ratio of the display screen and the aspect ratio of the ultrasound image, a partial region of the ultrasound image in the depth direction is not displayed on the display screen in some cases. FIG. 8A illustrates an example of a case where a partial region on the lower side of the ultrasound image in the depth direction is not displayed on the display screen, that is, a case where a hidden region is present in a part on the lower side of the ultrasound image in the depth direction.

In this case, the posture sensor 33 detects that the monitor 41 is in the laterally long posture.

On the other hand, as illustrated in FIG. 8A, in a case where a partial region on the lower side of the ultrasound image in the depth direction is not displayed on the display screen, the hidden region detection unit 61 detects that a hidden region is present in a part on the lower side of the ultrasound image in the depth direction.

In addition, the blood vessel in the ultrasound image is detected by the blood vessel detection unit 63.

Then, in a case where it is detected that a hidden region is present in a part on the lower side of the ultrasound image in the depth direction and it is detected that a blood vessel is present in the hidden region, the orientation suggestion unit 65 suggests to change the monitor 41 to the vertically long posture.

Accordingly, in a case where the monitor 41 is changed to the vertically long posture by the user, the posture sensor 33 detects that the changed posture of the monitor 41 is the vertically long posture, and the display control unit 43 displays the ultrasound image on the basis of the monitor 41 in the vertically long posture.

FIG. 8B illustrates a positional relationship between the display screen 72 in a case where the monitor 41 is in the vertically long posture and the ultrasound image 71 displayed on the display screen 72, in the second specific example. In this case, by the display control unit 43, the vertically long ultrasound image is displayed on the display screen without changing the aspect ratio of the ultrasound image. Note that the display control in this case is not particularly limited, and the ultrasound image may be displayed in any manner.

Similarly, even though there are many blood vessels in the ultrasound image in the depth direction, in a case where a partial region of the ultrasound image in the depth direction is not displayed on the display screen due to the laterally long posture of the monitor 41, the blood vessel in the partial region of the ultrasound image in the depth direction, which is not displayed in a case where the monitor 41 is in the laterally long posture, can be displayed by changing the monitor 41 to the vertically long posture, and therefore, it is possible for the user to easily check the blood vessel in the ultrasound image in the depth direction.

Note that, FIG. 8A illustrates an example of a case where the ultrasound image is displayed by being enlarged until the size of the vertically long ultrasound image in the width direction matches the size of the laterally long display screen in the left and right direction of the monitor 41 in the laterally long posture, but the invention is not limited thereto, and can be similarly applied to a case where the ultrasound image is displayed by being enlarged until the size of the vertically long ultrasound image in the width direction matches the size of the vertically long display screen in the left and right direction of the monitor 41 in the vertically long posture.

Figure 9A:
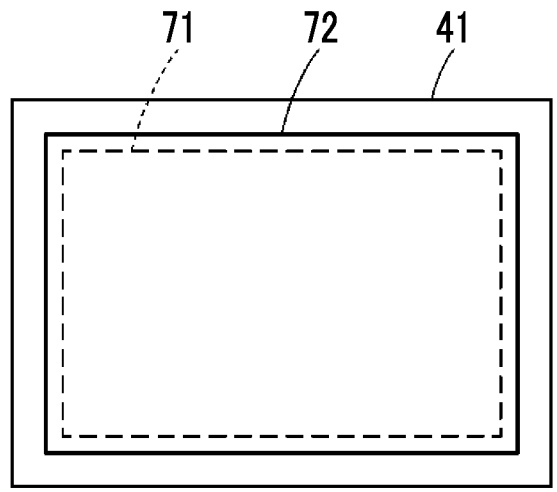
FIG. 9A is a conceptual diagram illustrating a positional relationship between a display screen in a case where a monitor is in a laterally long posture and an ultrasound image displayed on the display screen, in a third specific example.
Figure 9B:
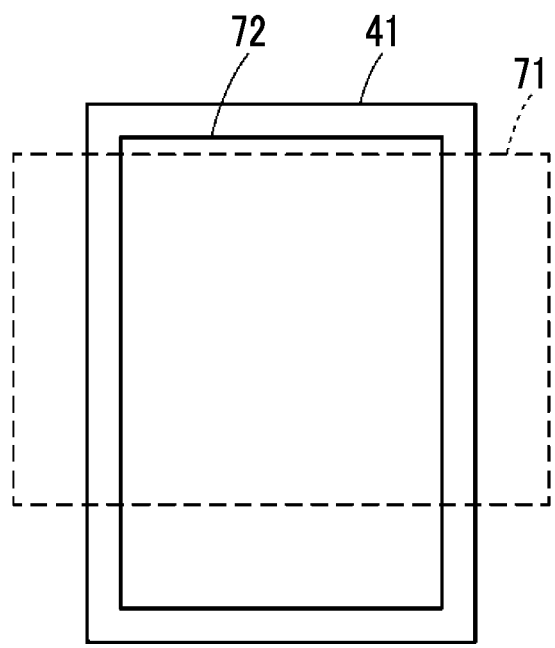
FIG. 9B is a conceptual diagram illustrating a positional relationship between a display screen in a case where a monitor is in a vertically long posture and an ultrasound image displayed on the display screen, in the third specific example.

FIGS. 9A and 9B are conceptual diagrams of a third specific example illustrating a positional relationship between the display screen and the ultrasound image displayed on the display screen.

In the third specific example, the aspect ratio of the display screen is the same as the aspect ratio of the laterally long ultrasound image, and in a case where the posture of the monitor 41 is changed between the laterally long posture and the vertically long posture, that is, in a case where the posture of the monitor 41 is changed from the laterally long posture to the vertically long posture or from the vertically long posture to the laterally long posture, the display control unit 43 performs control such that the ultrasound image is displayed on the display screen without changing the magnification ratio and the aspect ratio of the ultrasound image.

FIG. 9A illustrates a positional relationship between the display screen 72 in a case where the monitor 41 is in the laterally long posture and the ultrasound image 71 displayed on the display screen 72, in the third specific example. In this case, by the display control unit 43, the laterally long ultrasound image is displayed on the display screen without changing the aspect ratio of the ultrasound image. Note that the display control in this case is not particularly limited, and the ultrasound image may be displayed in any manner.

In a case where the monitor 41 is changed from the laterally long posture illustrated in FIG. 9A to the vertically long posture illustrated in FIG. 9B by the user, the posture sensor 33 detects that the changed posture of the monitor 41 is the vertically long posture, and the display control unit 43 displays the ultrasound image on the basis of the monitor 41 in the vertically long posture.

FIG. 9B illustrates a positional relationship between the display screen 72 in a case where the monitor 41 is in the vertically long posture and the ultrasound image 71 displayed on the display screen 72, in the third specific example. In a case where the monitor 41 is changed from the laterally long posture to the vertically long posture, by the display control unit 43, the laterally long ultrasound image is displayed on the display screen without changing the magnification ratio and the aspect ratio of the ultrasound image.

Even in a case where the ultrasound image is displayed as illustrated in FIG. 9B, depending on the difference between the aspect ratio of the display screen and the aspect ratio of the ultrasound image, a partial region of the ultrasound image in the width direction is not displayed on the display screen in some cases. FIG. 9B illustrates an example of a case where a part on both sides of the ultrasound image in the width direction is not displayed on the display screen, that is, a case where a hidden region is present in a part on both sides of the ultrasound image in the width direction.

In this case, the posture sensor 33 detects that the monitor 41 is in the vertically long posture.

On the other hand, as illustrated in FIG. 9B, in a case where it is detected that the posture of the monitor 41 is changed from the laterally long posture to the vertically long posture and a partial region on both sides of the ultrasound image in the width direction is not displayed on the display screen, the hidden region detection unit 61 detects that a hidden region is present in a part on both sides of the ultrasound image in the width direction.

In addition, the blood vessel in the ultrasound image is detected by the blood vessel detection unit 63.

Then, in a case where it is detected that a hidden region is present in a part on both sides of the ultrasound image in the width direction and it is detected that a blood vessel is present in the hidden region, the orientation suggestion unit 65 suggests to change the monitor 41 to the laterally long posture.

Accordingly, in a case where the monitor 41 is changed to the laterally long posture by the user, the posture sensor 33 detects that the changed posture of the monitor 41 is the laterally long posture, and the display control unit 43 displays the ultrasound image as illustrated in FIG. 9A on the basis of the monitor 41 in the laterally long posture.

In this manner, in a case where a partial region of the ultrasound image in the width direction is not displayed on the display screen due to the vertically long posture of the monitor 41, the blood vessel in the partial region of the ultrasound image in the width direction, which is not displayed in a case where the monitor 41 is in the vertically long posture, can be displayed by changing the monitor 41 to the laterally long posture, and therefore, it is possible for the user to easily check the blood vessel in the ultrasound image in the width direction.

Figure 10A:
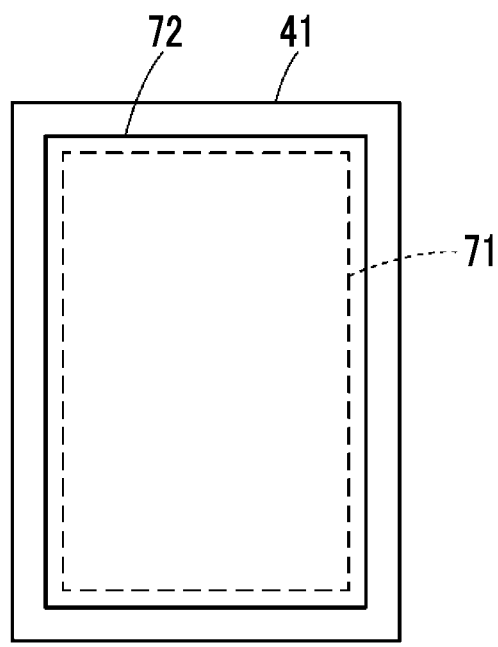
FIG. 10A is a conceptual diagram illustrating a positional relationship between a display screen in a case where a monitor is in a vertically long posture and an ultrasound image displayed on the display screen, in a fourth specific example.
Figure 10B:
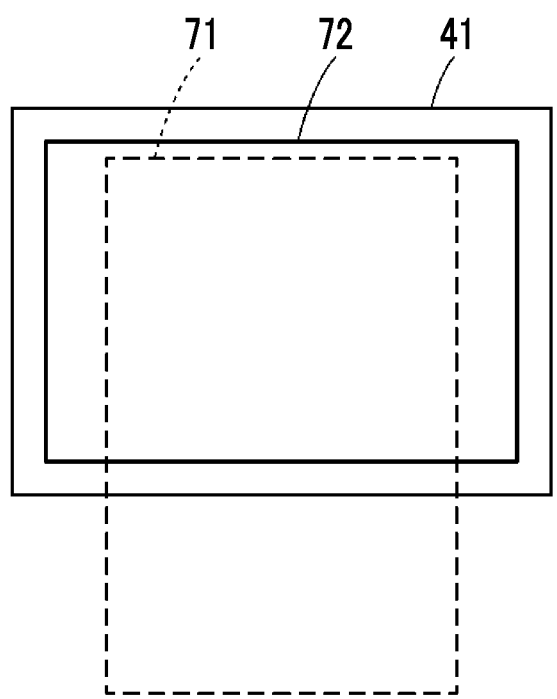
FIG. 10B is a conceptual diagram illustrating a positional relationship between a display screen in a case where a monitor is in a laterally long posture and an ultrasound image displayed on the display screen, in the fourth specific example.

FIGS. 10A and 10B are conceptual diagrams of a fourth specific example illustrating a positional relationship between the display screen and the ultrasound image displayed on the display screen.

In the fourth specific example, the aspect ratio of the display screen is the same as the aspect ratio of the vertically long ultrasound image, and in a case where the posture of the monitor 41 is changed between the vertically long posture and the laterally long posture, the display control unit 43 performs control such that the ultrasound image is displayed on the display screen without changing the magnification ratio and the aspect ratio of the ultrasound image.

FIG. 10A illustrates a positional relationship between the display screen 72 in a case where the monitor 41 is in the vertically long posture and the ultrasound image 71 displayed on the display screen 72, in the fourth specific example. In this case, by the display control unit 43, the vertically long ultrasound image is displayed on the display screen without changing the aspect ratio of the ultrasound image. Note that the display control in this case is not particularly limited, and the ultrasound image may be displayed in any manner.

In a case where the monitor 41 is changed from the vertically long posture illustrated in FIG. 10A to the laterally long posture illustrated in FIG. 10B by the user, the posture sensor 33 detects that the changed posture of the monitor 41 is the laterally long posture, and the display control unit 43 displays the ultrasound image on the basis of the monitor 41 in the laterally long posture.

FIG. 10B illustrates a positional relationship between the display screen 72 in a case where the monitor 41 is in the laterally long posture and the ultrasound image 71 displayed on the display screen 72, in the fourth specific example. In a case where the monitor 41 is changed from the vertically long posture to the laterally long posture, by the display control unit 43, the vertically long ultrasound image is displayed on the display screen without changing the magnification ratio and the aspect ratio of the ultrasound image.

Even in a case where the ultrasound image is displayed as illustrated in FIG. 10B, depending on the difference between the aspect ratio of the display screen and the aspect ratio of the ultrasound image, a partial region of the ultrasound image in the depth direction is not displayed on the display screen in some cases. FIG. 10B illustrates an example of a case where a part on the lower side of the ultrasound image in the depth direction is not displayed on the display screen, that is, a case where a hidden region is present in a part on the lower side of the ultrasound image in the depth direction.

In this case, the posture sensor 33 detects that the monitor 41 is in the laterally long posture.

On the other hand, as illustrated in FIG. 10B, in a case where it is detected that the posture of the monitor 41 is changed from the vertically long posture to the laterally long posture and a partial region on the lower side of the ultrasound image in the depth direction is not displayed on the display screen, the hidden region detection unit 61 detects that a hidden region is present in a part on the lower side of the ultrasound image in the depth direction.

In addition, the blood vessel in the ultrasound image is detected by the blood vessel detection unit 63.

Then, in a case where it is detected that a hidden region is present in a part on the lower side of the ultrasound image in the depth direction and it is detected that a blood vessel is present in the hidden region, the orientation suggestion unit 65 suggests to change the monitor 41 to the vertically long posture.

Accordingly, in a case where the monitor 41 is changed to the vertically long posture by the user, the posture sensor 33 detects that the changed posture of the monitor 41 is the vertically long posture, and the display control unit 43 displays the ultrasound image as illustrated in FIG. 10A on the basis of the monitor 41 in the vertically long posture.

In this manner, in a case where a partial region of the ultrasound image in the depth direction is not displayed on the display screen due to the laterally long posture of the monitor 41, the blood vessel in the partial region of the ultrasound image in the depth direction, which is not displayed in a case where the monitor 41 is in the laterally long posture, can be displayed by changing the monitor 41 to the vertically long posture, and therefore, it is possible for the user to easily check the blood vessel in the ultrasound image in the depth direction.

Figure 11A:
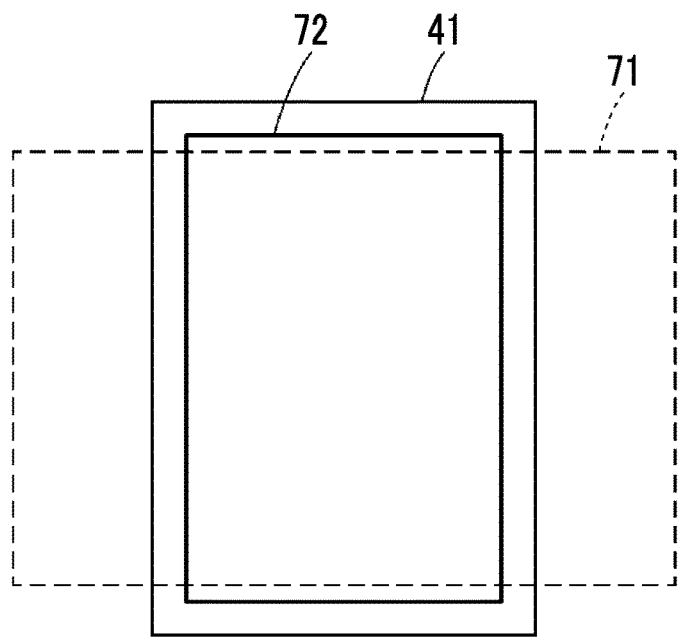
FIG. 11A is a conceptual diagram illustrating a positional relationship between a display screen in a case where a monitor is in a vertically long posture and an ultrasound image displayed on the display screen, in a fifth specific example.
Figure 11B:
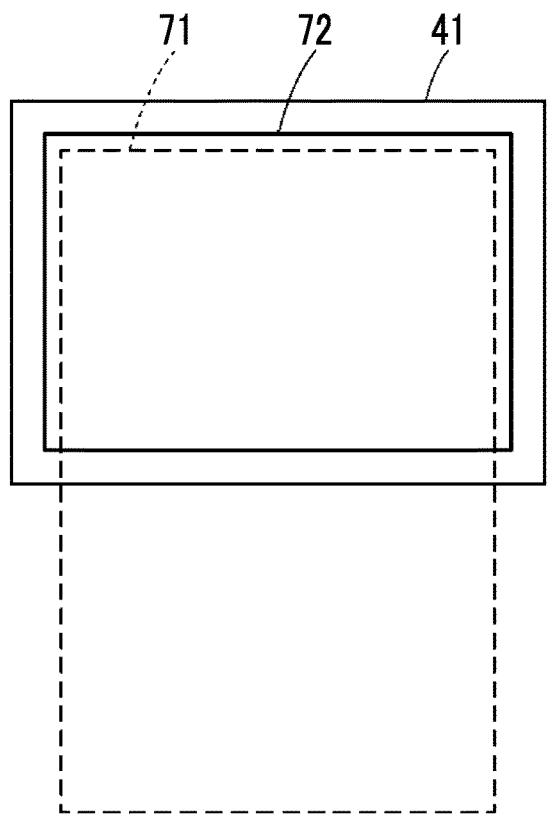
FIG. 11B is a conceptual diagram illustrating a positional relationship between a display screen in a case where a monitor is in a laterally long posture and an ultrasound image displayed on the display screen, in the fifth specific example.
Figure 12A:
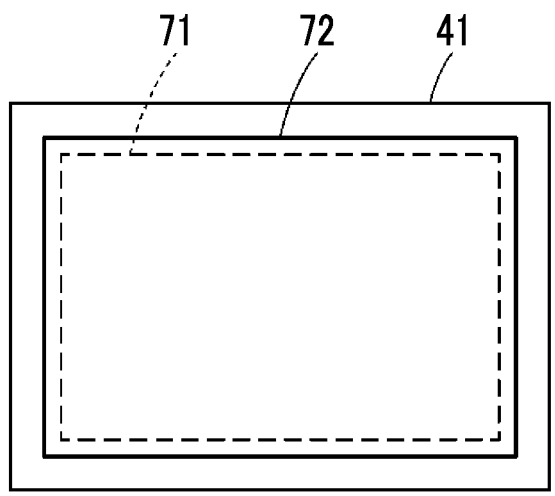
FIG. 12A is a conceptual diagram illustrating a state where a laterally long ultrasound image is displayed to fit within a display screen of a monitor in a laterally long posture.
Figure 12B:
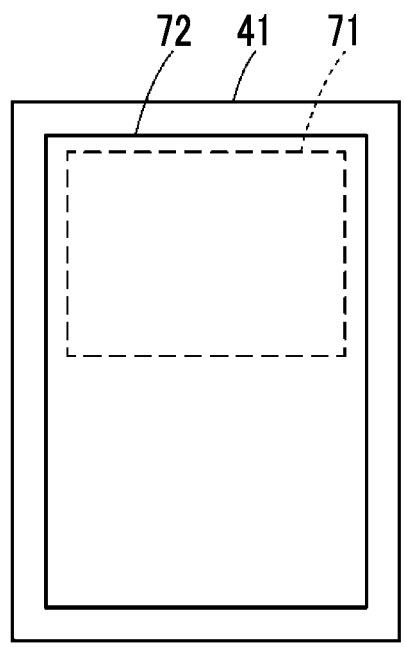
FIG. 12B is a conceptual diagram illustrating a state where a laterally long ultrasound image is displayed in a reduced manner such that the ultrasound image fits within a display screen of a monitor in a vertically long posture.

FIGS. 11A and 11B are conceptual diagrams of a fifth specific example illustrating a positional relationship between the display screen and the ultrasound image displayed on the display screen.

In the fifth specific example, the display control unit 43 performs control such that, in a case where it is detected that the monitor 41 is in the vertically long posture, the ultrasound image is displayed by being enlarged until the size of the ultrasound image in the depth direction matches the size of the display screen in the up and down direction without changing the aspect ratio of the ultrasound image, and in a case where it is detected that the monitor 41 is in the laterally long posture, the ultrasound image is displayed by being enlarged until the size of the ultrasound image in the width direction matches the size of the display screen in the left and right direction without changing the aspect ratio of the ultrasound image.

FIG. 11A illustrates a positional relationship between the display screen 72 in a case where the monitor 41 is in the vertically long posture and the ultrasound image 71 displayed on the display screen 72, in the fifth specific example. In this case, by the display control unit 43, the ultrasound image is displayed by being enlarged until the size of the laterally long ultrasound image in the depth direction matches the size of the display screen in the up and down direction without changing the aspect ratio of the ultrasound image.

Even in a case where the ultrasound image is displayed as illustrated in FIG. 11A, depending on the difference between the aspect ratio of the display screen and the aspect ratio of the ultrasound image, a partial region of the ultrasound image in the width direction is not displayed on the display screen in some cases. FIG. 11A illustrates an example of a case where a part on both sides of the ultrasound image in the width direction is not displayed on the display screen, that is, a case where a hidden region is present in a part on both sides of the ultrasound image in the width direction.

In this case, the posture sensor 33 detects that the monitor 41 is in the vertically long posture.

On the other hand, as illustrated in FIG. 11A, in a case where it is detected that the monitor 41 is in the vertically long posture and a partial region on both sides of the ultrasound image in the width direction is not displayed on the display screen, the hidden region detection unit 61 detects that a hidden region is present in a part on both sides of the ultrasound image in the width direction.

In addition, the blood vessel in the ultrasound image is detected by the blood vessel detection unit 63.

Then, in a case where it is detected that a hidden region is present in a part on both sides of the ultrasound image in the width direction and it is detected that a blood vessel is present in the hidden region, the orientation suggestion unit 65 suggests to change the monitor 41 to the laterally long posture.

Accordingly, in a case where the monitor 41 is changed to the laterally long posture by the user, the posture sensor 33 detects that the changed posture of the monitor 41 is the laterally long posture, and the display control unit 43 displays the ultrasound image on the basis of the monitor 41 in the laterally long posture.

FIG. 11B illustrates a positional relationship between the display screen 72 in a case where the monitor 41 is in the laterally long posture and the ultrasound image 71 displayed on the display screen 72, in the fifth specific example. In this case, by the display control unit 43, the ultrasound image is displayed by being enlarged until the size of the vertically long ultrasound image in the width direction matches the size of the display screen in the left and right direction without changing the aspect ratio of the ultrasound image.

In this manner, in a case where a partial region of the ultrasound image in the width direction is not displayed on the display screen due to the vertically long posture of the monitor 41, the blood vessel in the partial region of the ultrasound image in the width direction, which is not displayed in a case where the monitor 41 is in the vertically long posture, can be displayed by changing the monitor 41 to the laterally long posture, and therefore, it is possible for the user to easily check the blood vessel in the ultrasound image in the width direction.

Note that a case where the posture of the monitor 41 is changed from the vertically long posture illustrated in FIG. 11A to the laterally long posture illustrated in FIG. 11B has been described as an example, but the operation is similar even in a case where the posture of the monitor 41 is changed from the laterally long posture illustrated in FIG. 11B to the vertically long posture illustrated in FIG. 11A.

In the example illustrated in FIGS. 11A and 11B, in a case where a hidden region is generated in a case where the monitor 41 is in the vertically long posture illustrated in FIG.

11A and a hidden region is generated in a case where the monitor 41 is in the laterally long posture illustrated in FIG. 11B, changing the orientation of the monitor 41 may be suggested on the basis of the number of blood vessels in the hidden region in each of the case where the monitor 41 is in the vertically long posture and the case where the monitor 41 is in the laterally long posture.

In this case, the posture sensor 33 detects that the orientation of the monitor 41.

In addition, the hidden region detection unit 61 detects whether or not a hidden region is generated in each of a case where the monitor 41 is in the vertically long posture and a case where the monitor 41 is in the laterally long posture.

Subsequently, in a case where it is detected that a hidden region is generated in each of a case where the monitor 41 is in the vertically long posture and a case where the monitor 41 is in the laterally long posture, the blood vessel detection unit 63 detects the blood vessel in the hidden region in each of the case where the monitor 41 is in the vertically long posture and the case where the monitor 41 is in the laterally long posture.

Then, in a case where it is detected that the monitor 41 is in one orientation of the vertically long posture or the laterally long posture and the number of blood vessels in the hidden region in a case where the monitor 41 is in the other orientation is smaller than the number of blood vessels in the hidden region in a case where the monitor 41 is in the one orientation, the orientation suggestion unit 65 suggests to change the monitor 41 to the other orientation.

That is, in a case where it is detected that the monitor 41 is in the vertically long posture and the number of blood vessels in the hidden region in a case where the monitor 41 is in the laterally long posture is smaller than the number of blood vessels in the hidden region in a case where the monitor 41 is in the vertically long posture, the orientation suggestion unit 65 suggests to change the monitor 41 to the laterally long posture.

On the other hand, in a case where it is detected that the monitor 41 is in the laterally long posture and the number of blood vessels in the hidden region in a case where the monitor 41 is in the vertically long posture is smaller than the number of blood vessels in the hidden region in a case where the monitor 41 is in the laterally long posture, the orientation suggestion unit 65 suggests to change the monitor 41 to the vertically long posture.

In this manner, by changing the orientation of the monitor 41 so that the number of blood vessels in the hidden region is reduced, it is possible to reduce the number of blood vessels in the hidden region and increase the number of blood vessels to be displayed in the display region.

In addition, in the example illustrated in FIGS. 11A and 11B, in a case where a hidden region is generated in each of a case where the monitor 41 is in the vertically long posture illustrated in FIG. 11A and a case where the monitor 41 is in the laterally long posture illustrated in FIG. 11B, changing the orientation of the monitor 41 may be suggested on the basis of the type of the blood vessels in the display region and the hidden region of the ultrasound image, that is, whether the blood vessel is an artery or a vein.

In this case, the posture sensor 33 detects that the orientation of the monitor 41.

On the other hand, the hidden region detection unit 61 detects whether or not a hidden region is generated in each of a case where the monitor 41 is in the vertically long posture and a case where the monitor 41 is in the laterally long posture.

In addition, the blood vessel in the ultrasound image is detected by the blood vessel detection unit 63. Furthermore, in a case where it is detected that a hidden region is generated in each of a case where the monitor 41 is in the vertically long posture illustrated and a case where the monitor 41 is in the laterally long posture and it is detected that a blood vessel is present in each of the display region and the hidden region of the ultrasound image, the blood vessel detection unit 63 discriminates whether the type of the blood vessel in each of the display region and the hidden region is an artery or a vein.

Then, the orientation suggestion unit 65 suggests to change the orientation of the monitor 41 on the basis of the type of the blood vessel in the display region and the type of the blood vessel in the hidden region.

In a case where the blood vessel puncture is performed, it is important to check whether or not an artery is present below the vein and to take care that the puncture needle does not reach the artery below the vein. Therefore, it may be suggested to change the orientation of the monitor 41 on the basis of the positional relationship between the vein and the artery.

For example, in a case where a vein is present in the display region in a case where the monitor 41 is in the laterally long posture, it may be detected whether or not an artery is present below the vein in the hidden region.

The operations of the posture sensor 33, the hidden region detection unit 61, and the blood vessel detection unit 63 in this case are the same as those in the fifth specific example described above.

Then, in a case where it is detected that the monitor 41 is in the laterally long posture, and it is discriminated that a vein is present in the display region in a case where the monitor 41 is in the laterally long posture and that an artery is present in the hidden region in a case where the monitor 41 is in the laterally long posture, the orientation suggestion unit 65 suggests to change the monitor 41 to the vertically long posture.

Accordingly, even in a case where the artery below the vein is not displayed on the display screen due to the laterally long posture of the monitor 41, the artery below the vein can be displayed on the display screen by changing the monitor 41 to the vertically long posture. Therefore, in a case where the blood vessel puncture is performed, it is possible for the user to check whether or not an artery is present below the vein, and to perform the technique such that the puncture needle does not reach the artery below the vein.

In addition, in a case where a vein is present in the display region in a case where the monitor 41 is in the vertically long posture, it may be detected whether or not a vein is also present in the hidden region.

The operations of the posture sensor 33, the hidden region detection unit 61, and the blood vessel detection unit 63 in this case are the same as those in the fifth specific example described above.

Then, in a case where it is detected that the monitor 41 is in the vertically long posture, and it is discriminated that a vein is present in the display region in a case where the monitor 41 is in the vertically long posture and that a vein is present in the hidden region in a case where the monitor 41 is in the vertically long posture, the orientation suggestion unit 65 suggests to change the monitor 41 to the laterally long posture.

Accordingly, even in a case where the vein in the left and right direction of the vein is not displayed on the display screen due to the vertically long posture of the monitor 41, the vein in the left and right direction of the vein can be displayed on the display screen by changing the monitor 41 to the laterally long posture. Therefore, in a case where the blood vessel puncture is performed, it is possible for the user to check more veins and to select a better vein as the blood vessel as the puncture target.

In addition, in a case where an artery is present in the display region, it may be detected whether or not a vein is present in the hidden region.

The operations of the posture sensor 33 and the hidden region detection unit 61 in this case are the same as those in the fifth specific example described above.

Subsequently, in a case where it is discriminated that an artery is present in the display region, the blood vessel detection unit 63 discriminates whether or not a vein is present in the hidden region in each of a case where the monitor is in one orientation of the vertically long posture and the laterally long posture and a case where the monitor 41 is in the other orientation, on the basis of the position of the artery in the display region and the anatomical structure around the artery in the display region.

Then, in a case where it is discriminated that no vein is present in the hidden region in a case where the monitor 41 is in the one orientation and that a vein is present in the hidden region in a case where the monitor 41 is in the other orientation, the orientation suggestion unit 65 suggests to change the monitor 41 to the other orientation. Alternatively, in a case where the number of veins in the hidden region in a case where the monitor 41 is in the other orientation is greater than the number of veins in the hidden region in a case where the monitor 41 is in the one orientation, the orientation suggestion unit 65 may suggest to change the monitor 41 to the other orientation.

Accordingly, even in a case where the vein is not displayed on the display screen due to the orientation of the monitor 41, the vein can be displayed on the display screen by changing the orientation of the monitor 41, and thus it is possible for the user to easily find the vein as the puncture target.

The first to fifth specific examples described above are examples in which the ultrasound image is automatically enlarged and displayed by the display control unit 43, but the user can manually enlarge and display as a sixth specific example. Even in this case, the hidden region may be generated depending on the difference between the aspect ratio of the display screen and the aspect ratio of the ultrasound image.

In a case where the ultrasound image is manually enlarged and displayed by the user, the display control unit 43 performs control such that the ultrasound image is enlarged and displayed without changing the aspect ratio of the ultrasound image according to an instruction from the user.

In this case, the posture sensor 33 detects that the orientation of the monitor 41.

On the other hand, by the user manually enlarging and displaying the ultrasound image, in a case where a partial region of the ultrasound image in the depth direction is not displayed on the display screen, the hidden region detection unit 61 detects that a hidden region is present in a part of the ultrasound image in the depth direction, and in a case where a partial region of the ultrasound image in the width direction is not displayed on the display screen, the hidden region detection unit 61 detects that a hidden region is present in a part of the ultrasound image in the width direction.

In addition, the blood vessel in the ultrasound image is detected by the blood vessel detection unit 63.

Then, in a case where it is detected that a hidden region is present in a part of the ultrasound image in the depth direction and it is detected that a blood vessel is present in the hidden region, the orientation suggestion unit 65 suggests to change the orientation of the monitor 41. On the other hand, in a case where it is detected that a hidden region is present in a part of the ultrasound image in the width direction and it is detected that a blood vessel is present in the hidden region, the orientation suggestion unit 65 suggests to change the orientation of the monitor 41.

In a case where it is detected that a hidden region is present in a part of the ultrasound image in each of the depth direction and the width direction and it is detected that a blood vessel is present in each hidden region, the orientation suggestion unit 65 may suggest to change the orientation of the monitor 41 to an orientation in which the area of the hidden region itself is reduced, or may suggest to change the orientation of the monitor 41 to an orientation in which the number of blood vessels in the hidden region is reduced.

In addition, in this case, the orientation suggestion unit 65 may suggest to change the orientation of the monitor 41 on the basis of the type of the blood vessels in the display region and the hidden region of the ultrasound image, that is, whether the blood vessel is an artery or a vein.

For example, in a case where the monitor 41 is in the laterally long posture, a hidden region is present in a part on the lower side of the ultrasound image in the depth direction, and an artery is present in the hidden region, it may be suggested to change the monitor 41 to the vertically long posture. Accordingly, since the artery in the hidden region can be displayed, it is possible to reduce a risk of medical accidents caused by advancing the puncture needle too far and puncturing an artery. Note that, in a case where no artery is present in the hidden region, the monitor 41 may remain in the laterally long posture, and there is no need to suggest to change the orientation of the monitor 41.

In addition, for example, in a case where the monitor 41 is in the vertically long posture, a hidden region is present in a part of the ultrasound image in the width direction, and a vein is present in the hidden region, it may be suggested to change the monitor 41 to the laterally long posture. Accordingly, since the vein in the hidden region can be displayed, it is possible to search for a better vein as the blood vessel as the puncture target. Note that, even in a case where an artery is present in the hidden region, since the puncture needle does not advance in the width direction of the ultrasound image, the monitor 41 may remain in the vertically long posture, and there is no need to suggest to change the orientation of the monitor 41.

Accordingly, even in a case where the ultrasound image is manually enlarged and displayed by the user and the hidden region is generated, it is possible to display the blood vessel in the hidden region on the display screen by changing the orientation of the monitor 41.

Note that the specific examples in a case where the hidden region is generated in the ultrasound image have been described, but it is needless to say that the present invention is not limited to the specific examples and there are various cases in which the hidden region is generated even in cases other than the specific examples described above.

The present invention is not limited to the handheld ultrasound diagnostic apparatus, and can be similarly applied to a stationary ultrasound diagnostic apparatus including a monitor of which the orientation can be changed to a vertically long posture or a laterally long posture by the user rotating the monitor by 90 degrees, or a portable ultrasound diagnostic apparatus which includes a monitor of which the orientation can be similarly changed to a vertically long posture or a laterally long posture, and of which the apparatus main body 3 is realized by a laptop terminal device. In a case of a stationary or portable ultrasound diagnostic apparatus, the posture sensor is built in the monitor, and detects whether the orientation (posture) of the monitor is a laterally long posture or a vertically long posture.

In addition, as illustrated in FIG. 1, the apparatus main body 3 may include the ultrasound image generation unit 31, but the present invention is not limited thereto, and the entire ultrasound image generation unit 31 or only the signal processing unit 21 may be provided on the ultrasound probe 1 side.

In the apparatus of the embodiment of the present invention, the hardware configurations of the processing units executing various kinds of processing such as the transmission and reception circuit 13, the ultrasound image generation unit 31, the orientation suggestion processing unit 35, the display control unit 43, and the apparatus control unit 47 may be dedicated hardware, or may be various processors or computers that execute programs.

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing specific processing such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor realizing the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the embodiment of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: apparatus main body
11: transducer array
13: transmission and reception circuit
15: battery
21: signal processing unit
23: DSC
25: image processing unit
31: ultrasound image generation unit
33: posture sensor
35: orientation suggestion processing unit
41: monitor
43: display control unit
45: input device
47: apparatus control unit
49: processor
51: pulser
53: amplification unit
55: AD conversion unit
57: beam former
61: hidden region detection unit
63: blood vessel detection unit
65: orientation suggestion unit
71: ultrasound image
72: display screen

What is claimed is:
1. An ultrasound diagnostic apparatus comprising:
a monitor which has a rectangular display screen, and of which an orientation is changeable to a vertically long posture or a laterally long posture;
a posture sensor that detects whether the orientation of the monitor is the vertically long posture or the laterally long posture; and
a processor,
wherein the processor is configured to display an ultrasound image on the display screen on the basis of the orientation of the monitor, detect whether or not a hidden region that is not displayed on the display screen is present in the ultrasound image, detect a blood vessel in the ultrasound image, and suggest to change the orientation of the monitor in a case where it is detected that the hidden region is present and it is detected that the blood vessel is present in the hidden region.
2. The ultrasound diagnostic apparatus according to claim 1,
wherein the processor is configured to detect whether or not the hidden region is present on the basis of at least one of an aspect ratio of the display screen, an aspect ratio of the ultrasound image, a magnification ratio of the ultrasound image, or the orientation of the monitor.
3. The ultrasound diagnostic apparatus according to claim 2,
wherein, in a case where it is detected that the hidden region is present, the processor is configured to detect a blood vessel in the hidden region.
4. The ultrasound diagnostic apparatus according to claim 2, wherein the processor is configured to perform control such that the ultrasound image is displayed by being enlarged until a size of the ultrasound image in a depth direction matches a size of the display screen in an up and down direction without changing an aspect ratio of the ultrasound image, regardless of the orientation of the monitor, and in a case where a partial region of the ultrasound image in a width direction is not displayed on the display screen, the processor is configured to detect that the hidden region is present in a part of the ultrasound image in the width direction.

5. The ultrasound diagnostic apparatus according to claim 2,
wherein the processor is configured to perform control such that the ultrasound image is displayed by being enlarged until a size of the ultrasound image in a width direction matches a size of the display screen in a left and right direction without changing an aspect ratio of the ultrasound image, regardless of the orientation of the monitor, and in a case where a partial region of the ultrasound image in a depth direction is not displayed on the display screen, the processor is configured to detect that the hidden region is present in a part of the ultrasound image in the depth direction.

6. The ultrasound diagnostic apparatus according to claim 2,
wherein an aspect ratio of the display screen is the same as an aspect ratio of a laterally long ultrasound image, in a case where the monitor is changed between the laterally long posture and the vertically long posture, the processor is configured to perform control such that the ultrasound image is displayed on the display screen without changing the aspect ratio and a magnification ratio of the ultrasound image, and in a case where it is detected that the monitor is changed from the laterally long posture to the vertically long posture and a partial region of the ultrasound image in a width direction is not displayed on the display screen, the processor is configured to detect that the hidden region is present in a part of the ultrasound image in the width direction.

7. The ultrasound diagnostic apparatus according to claim 2,
wherein an aspect ratio of the display screen is the same as an aspect ratio of a vertically long ultrasound image, in a case where the monitor is changed between the vertically long posture and the laterally long posture, the processor is configured to perform control such that the ultrasound image is displayed on the display screen without changing the aspect ratio and a magnification ratio of the ultrasound image, and in a case where it is detected that the monitor is changed from the vertically long posture to the laterally long posture and a partial region of the ultrasound image in a depth direction is not displayed on the display screen, the processor is configured to detect that the hidden region is present in a part of the ultrasound image in the depth direction.

8. The ultrasound diagnostic apparatus according to claim 1,
wherein, in a case where it is detected that the hidden region is present, the processor is configured to detect a blood vessel in the hidden region.

9. The ultrasound diagnostic apparatus according to claim 1,
wherein the processor is configured to perform control such that the ultrasound image is displayed by being enlarged until a size of the ultrasound image in a depth direction matches a size of the display screen in an up and down direction without changing an aspect ratio of the ultrasound image, regardless of the orientation of the monitor, and in a case where a partial region of the ultrasound image in a width direction is not displayed on the display screen, the processor is configured to detect that the hidden region is present in a part of the ultrasound image in the width direction.

10. The ultrasound diagnostic apparatus according to claim 1,
wherein the processor is configured to perform control such that the ultrasound image is displayed by being enlarged until a size of the ultrasound image in a width direction matches a size of the display screen in a left and right direction without changing an aspect ratio of the ultrasound image, regardless of the orientation of the monitor, and in a case where a partial region of the ultrasound image in a depth direction is not displayed on the display screen, the processor is configured to detect that the hidden region is present in a part of the ultrasound image in the depth direction.

11. The ultrasound diagnostic apparatus according to claim 1,
wherein an aspect ratio of the display screen is the same as an aspect ratio of a laterally long ultrasound image, in a case where the monitor is changed between the laterally long posture and the vertically long posture, the processor is configured to perform control such that the ultrasound image is displayed on the display screen without changing the aspect ratio and a magnification ratio of the ultrasound image, and in a case where it is detected that the monitor is changed from the laterally long posture to the vertically long posture and a partial region of the ultrasound image in a width direction is not displayed on the display screen, the processor is configured to detect that the hidden region is present in a part of the ultrasound image in the width direction.

12. The ultrasound diagnostic apparatus according to claim 1,
wherein an aspect ratio of the display screen is the same as an aspect ratio of a vertically long ultrasound image, in a case where the monitor is changed between the vertically long posture and the laterally long posture, the processor is configured to perform control such that the ultrasound image is displayed on the display screen without changing the aspect ratio and a magnification ratio of the ultrasound image, and in a case where it is detected that the monitor is changed from the vertically long posture to the laterally long posture and a partial region of the ultrasound image in a depth direction is not displayed on the display screen, the processor is configured to detect that the hidden region is present in a part of the ultrasound image in the depth direction.

13. The ultrasound diagnostic apparatus according to claim 1,
wherein the processor is configured to perform control such that, in a case where it is detected that the monitor is in the vertically long posture, the ultrasound image is displayed by being enlarged until a size of the ultrasound image in a depth direction matches a size of the display screen in an up and down direction without changing an aspect ratio of the ultrasound image, and in a case where it is detected that the monitor is in the laterally long posture, the ultrasound image is displayed by being enlarged until a size of the ultrasound image in a width direction matches a size of the display screen in a left and right direction without changing the aspect ratio of the ultrasound image, and in a case where it is detected that the monitor is in the vertically long posture and a partial region of the ultrasound image in the width direction is not displayed on the display screen, the processor is configured to detect that the hidden region is present in a part of the ultrasound image in the width direction, and in a case where it is detected that the monitor is in the laterally long posture and a partial region of the ultrasound image in the depth direction is not displayed on the display screen, the processor is configured to detect that the hidden region is present in a part of the ultrasound image in the depth direction.

14. The ultrasound diagnostic apparatus according to claim 13, wherein the processor is configured to detect whether or not the hidden region is generated in each of a case where the monitor is in the vertically long posture and a case where the monitor is in the laterally long posture, in a case where it is detected that the hidden region is generated in each of the case where the monitor is in the vertically long posture and the case where the monitor is in the laterally long posture, the processor is configured to detect a blood vessel in the hidden region in each of the case where the monitor is in the vertically long posture and the case where the monitor is in the laterally long posture, and in a case where it is detected that the monitor is in one orientation of the vertically long posture or the laterally long posture and the number of blood vessels in the hidden region in a case where the monitor is in the other orientation is smaller than the number of blood vessels in the hidden region in a case where the monitor is in the one orientation, the processor is configured to suggest to change the monitor to the other orientation.

15. The ultrasound diagnostic apparatus according to claim 13, wherein the processor is configured to detect whether or not the hidden region is generated in each of a case where the monitor is in the vertically long posture and a case where the monitor is in the laterally long posture, in a case where it is detected that the hidden region is generated in each of the case where the monitor is in the vertically long posture and the case where the monitor is in the laterally long posture and it is detected that a blood vessel is present in each of a display region displayed on the display screen and the hidden region of the ultrasound image, the processor is configured to discriminate whether a type of the blood vessel in each of the display region and the hidden region is an artery or a vein, and the processor is configured to suggest to change the orientation of the monitor on the basis of the type of the blood vessel in the display region and the type of the blood vessel in the hidden region.

16. The ultrasound diagnostic apparatus according to claim 15, wherein, in a case where it is detected that the monitor is in the laterally long posture and it is discriminated that a vein is present in the display region in a case where the monitor is in the laterally long posture and that an artery is present in the hidden region in a case where the monitor is in the laterally long posture, the processor is configured to suggest to change the monitor to the vertically long posture.

17. The ultrasound diagnostic apparatus according to claim 15, wherein, in a case where it is detected that the monitor is in the vertically long posture and it is discriminated that a vein is present in the display region in a case where the monitor is in the vertically long posture and that a vein is present in the hidden region in a case where the monitor is in the vertically long posture, the processor is configured to suggest to change the monitor to the laterally long posture.

18. The ultrasound diagnostic apparatus according to claim 15, wherein, in a case where it is discriminated that an artery is present in the display region, the processor is configured to discriminate whether or not a vein is present in the hidden region in each of a case where the monitor is in one orientation of the vertically long posture or the laterally long posture and a case where the monitor is in the other orientation, on the basis of a position of the artery in the display region and an anatomical structure around the artery in the display region, and in a case where it is discriminated that no vein is present in the hidden region in a case where the monitor is in the one orientation and that a vein is present in the hidden region in a case where the monitor is in the other orientation, the processor is configured to suggest to change the monitor to the other orientation.

19. The ultrasound diagnostic apparatus according to claim 1, wherein the processor is configured to perform control such that the ultrasound image is enlarged and displayed without changing an aspect ratio of the ultrasound image according to an instruction from a user, and in a case where the ultrasound image is enlarged and displayed so that a partial region of the ultrasound image in a depth direction is not displayed on the display screen, the processor is configured to detect that the hidden region is present in a part of the ultrasound image in the depth direction, and in a case where the ultrasound image is enlarged and displayed so that a partial region of the ultrasound image in a width direction is not displayed on the display screen, the processor is configured to detect that the hidden region is present in a part of the ultrasound image in the width direction.

20. A control method of an ultrasound diagnostic apparatus including a monitor which has a rectangular display screen, and of which an orientation is changeable to a vertically long posture or a laterally long posture, the control method comprising:

a step of detecting whether the orientation of the monitor is the vertically long posture or the laterally long posture, via a posture sensor;

a step of displaying an ultrasound image on the display screen on the basis of the orientation of the monitor, via a processor;

a step of detecting whether or not a hidden region that is not displayed on the display screen is present in the ultrasound image, via the processor;

a step of detecting a blood vessel in the ultrasound image, via the processor; and a step of suggesting to change the orientation of the monitor in a case where it is detected that the hidden region is present and it is detected that the blood vessel is present in the hidden region, via the processor.

* * * * *